United States Patent
Lab et al.

(10) Patent No.: US 11,213,324 B2
(45) Date of Patent: *Jan. 4, 2022

(54) APPARATUS AND METHOD FOR LIMITING A RANGE OF ANGULAR POSITIONS OF A SCREW

(71) Applicant: Seaspine, Inc., Carlsbad, CA (US)

(72) Inventors: Eric A. Lab, Wadsworth, OH (US);
Joel P. Bales, Garrettsville, OH (US);
Simon Gerhard Sjovold, North Canton, OH (US); Keun-Young Anthony Kim, Irvine, CA (US)

(73) Assignee: Theken Spine, LLC, Carlsbad, CA (US)

( * ) Notice: Subject to any disclaimer, the term of this patent is extended or adjusted under 35 U.S.C. 154(b) by 12 days.

This patent is subject to a terminal disclaimer.

(21) Appl. No.: 16/278,549

(22) Filed: Feb. 18, 2019

(65) Prior Publication Data

US 2019/0183538 A1 Jun. 20, 2019

Related U.S. Application Data

(60) Division of application No. 15/449,460, filed on Mar. 3, 2017, now Pat. No. 10,206,717, which is a division of application No. 14/797,702, filed on Jul. 13, 2015, now Pat. No. 9,707,014, which is a continuation of application No. 13/180,332, filed on Jul. 11, 2011, now Pat. No. 9,084,634.

(60) Provisional application No. 61/362,993, filed on Jul. 9, 2010.

(51) Int. Cl.
*A61B 17/70* (2006.01)

(52) U.S. Cl.
CPC ...... *A61B 17/7038* (2013.01); *A61B 17/7002* (2013.01); *A61B 17/7032* (2013.01); *A61B 17/7076* (2013.01); *A61B 17/7083* (2013.01)

(58) Field of Classification Search
CPC ............ A61B 17/7035; A61B 17/7038; A61B 17/7037
See application file for complete search history.

(56) References Cited

U.S. PATENT DOCUMENTS

| | | | |
|---|---|---|---|
| 2,699,774 | A | 1/1955 | Livingston |
| 4,653,481 | A | 3/1987 | Howland et al. |
| 4,719,905 | A | 1/1988 | Steffee |
| 4,805,602 | A | 2/1989 | Puno et al. |
| 4,950,269 | A | 8/1990 | Gaines, Jr. |

(Continued)

FOREIGN PATENT DOCUMENTS

| | | |
|---|---|---|
| WO | 0019923 | 4/2000 |
| WO | 0152758 | 7/2001 |

OTHER PUBLICATIONS

PCT/US2004/010319 International Preliminary Report on Patentability and Written Opinion dated Oct. 14, 2005, pp. 1-4.

(Continued)

*Primary Examiner* — Jan Christopher L Merene
(74) *Attorney, Agent, or Firm* — Middleton Reutlinger

(57) ABSTRACT

A spinal screw assembly is provided. The assembly may be provided with a screw and a movable head in which angulation of the screw relative to the movable head is constrained so that angulation within limits is allowed in one plane but lesser or no angulation is allowed in another plane. Methods to assemble the disclosed apparatus are also disclosed.

14 Claims, 34 Drawing Sheets

(56) References Cited

U.S. PATENT DOCUMENTS

| | | |
|---|---|---|
| 5,053,036 A | 10/1991 | Perren et al. |
| 5,085,660 A | 2/1992 | Lin |
| 5,108,395 A | 4/1992 | Laurain |
| 5,112,332 A | 5/1992 | Cozad et al. |
| 5,116,334 A | 5/1992 | Cozad et al. |
| 5,152,303 A | 10/1992 | Allen |
| 5,154,719 A | 10/1992 | Cotrel |
| 5,181,917 A | 1/1993 | Rogozinski |
| 5,196,013 A | 3/1993 | Harms et al. |
| 5,207,678 A | 5/1993 | Harms et al. |
| 5,261,911 A | 11/1993 | Carl |
| 5,281,223 A | 1/1994 | Ray |
| 5,324,290 A | 6/1994 | Zdeblick et al. |
| 5,330,473 A | 7/1994 | Howland |
| 5,380,325 A | 1/1995 | Lahille et al. |
| 5,382,248 A | 1/1995 | Jacobson et al. |
| 5,403,314 A | 4/1995 | Currier |
| 5,443,467 A | 8/1995 | Biedermann et al. |
| 5,466,237 A | 11/1995 | Byrd, III et al. |
| 5,474,555 A | 12/1995 | Puno et al. |
| 5,480,401 A | 1/1996 | Navas |
| 5,486,176 A | 1/1996 | Hildebrand et al. |
| 5,501,684 A | 3/1996 | Schlapfer et al. |
| 5,549,608 A | 8/1996 | Errico et al. |
| 5,554,157 A | 9/1996 | Errico et al. |
| 5,584,834 A | 12/1996 | Errico et al. |
| 5,586,984 A | 12/1996 | Errico et al. |
| 5,591,165 A | 1/1997 | Jackson |
| 5,591,235 A | 1/1997 | Kuslich |
| 5,601,552 A | 2/1997 | Cotrel |
| 5,615,965 A | 4/1997 | Saurat et al. |
| 5,620,443 A | 4/1997 | Gertzbein et al. |
| 5,624,442 A | 4/1997 | Mellinger et al. |
| 5,669,911 A | 9/1997 | Errico et al. |
| 5,672,176 A | 9/1997 | Biedermann et al. |
| 5,681,319 A | 10/1997 | Biedermann et al. |
| 5,683,391 A | 11/1997 | Boyd |
| 5,690,630 A | 11/1997 | Errico et al. |
| 5,713,900 A | 2/1998 | Benzel et al. |
| 5,716,356 A | 2/1998 | Biedermann et al. |
| 5,725,527 A | 3/1998 | Biedermann et al. |
| 5,728,098 A | 3/1998 | Sherman et al. |
| 5,733,285 A | 3/1998 | Errico et al. |
| 5,738,685 A | 4/1998 | Halm et al. |
| 5,752,957 A | 5/1998 | Ralph et al. |
| 5,782,833 A | 7/1998 | Haider |
| 5,797,911 A | 8/1998 | Sherman et al. |
| 5,800,435 A | 9/1998 | Errico et al. |
| 5,817,094 A | 10/1998 | Errico et al. |
| 5,863,293 A | 1/1999 | Richelsoph |
| 5,879,350 A | 3/1999 | Sherman et al. |
| 5,882,350 A | 3/1999 | Ralph et al. |
| 5,885,286 A | 3/1999 | Sherman et al. |
| 5,888,221 A | 3/1999 | Gelbard |
| 5,891,145 A | 4/1999 | Morrison et al. |
| 5,910,142 A | 6/1999 | Tatar |
| 5,925,047 A | 7/1999 | Errico et al. |
| 5,954,725 A | 9/1999 | Sherman et al. |
| 5,964,760 A | 10/1999 | Richelsoph |
| 5,989,254 A | 11/1999 | Katz |
| 5,997,539 A | 12/1999 | Errico et al. |
| 6,010,503 A | 1/2000 | Richelsoph et al. |
| 6,017,344 A | 1/2000 | Errico et al. |
| 6,019,759 A | 2/2000 | Rogozinski |
| 6,022,350 A | 2/2000 | Ganem |
| 6,048,343 A | 4/2000 | Mathis et al. |
| 6,050,997 A | 4/2000 | Mullane |
| 6,053,917 A | 4/2000 | Sherman et al. |
| 6,063,090 A | 5/2000 | Schlapfer |
| 6,074,391 A | 6/2000 | Metz-Stavenhagen et al. |
| 6,090,111 A | 7/2000 | Nichols |
| 6,113,601 A | 9/2000 | Tatar |
| 6,132,430 A | 10/2000 | Wagner |
| 6,132,432 A | 10/2000 | Richelsoph |
| 6,132,434 A | 10/2000 | Sherman et al. |
| 6,146,383 A | 11/2000 | Studer et al. |
| 6,183,473 B1 | 2/2001 | Ashman |
| 6,187,005 B1 | 2/2001 | Brace et al. |
| 6,206,879 B1 | 3/2001 | Marnay et al. |
| 6,210,376 B1 | 4/2001 | Grayson |
| 6,214,006 B1 | 4/2001 | Metz-Stavenhagen |
| 6,214,012 B1 | 4/2001 | Karpman et al. |
| RE37,161 E | 5/2001 | Michelson et al. |
| 6,226,548 B1 | 5/2001 | Foley et al. |
| 6,248,105 B1 | 6/2001 | Schlapfer et al. |
| 6,254,602 B1 | 7/2001 | Justis |
| 6,273,888 B1 | 8/2001 | Justis |
| 6,280,442 B1 | 8/2001 | Barker et al. |
| 6,280,443 B1 | 8/2001 | Gu et al. |
| 6,287,311 B1 | 9/2001 | Sherman et al. |
| 6,302,888 B1 | 10/2001 | Mellinger et al. |
| 6,309,391 B1 | 10/2001 | Crandall et al. |
| 6,355,040 B1 | 3/2002 | Richelsoph et al. |
| 6,361,535 B2 | 3/2002 | Jackson |
| RE37,665 E | 4/2002 | Ralph et al. |
| 6,368,321 B1 | 4/2002 | Jackson |
| 6,371,957 B1 | 4/2002 | Amrein et al. |
| 6,375,657 B1 | 4/2002 | Doubler et al. |
| 6,413,257 B1 | 7/2002 | Lin et al. |
| 6,416,515 B1 | 7/2002 | Wagner |
| 6,440,137 B1 | 8/2002 | Horvath et al. |
| 6,454,768 B1 | 9/2002 | Jackson |
| 6,454,773 B1 | 9/2002 | Sherman et al. |
| 6,458,132 B2 | 10/2002 | Choi |
| 6,471,705 B1 | 10/2002 | Biedermann et al. |
| 6,475,218 B2 | 11/2002 | Gournay et al. |
| 6,485,491 B1 | 11/2002 | Farris et al. |
| 6,485,494 B1 | 11/2002 | Haider |
| 6,488,681 B2 | 12/2002 | Martin et al. |
| 6,537,276 B2 | 3/2003 | Metz-Stavenhagen |
| 6,540,748 B2 | 4/2003 | Lombardo |
| 6,547,790 B2 | 4/2003 | Harkey, III et al. |
| 6,554,832 B2 | 4/2003 | Shluzas |
| 6,554,834 B1 | 4/2003 | Crozet et al. |
| 6,565,565 B1 | 5/2003 | Yuan et al. |
| 6,565,567 B1 | 5/2003 | Haider |
| 6,582,436 B2 | 6/2003 | Schlapfer et al. |
| 6,595,992 B1 | 7/2003 | Wagner et al. |
| 6,613,050 B1 | 9/2003 | Wagner et al. |
| 6,623,485 B2 | 9/2003 | Doubler et al. |
| 6,626,906 B1 | 9/2003 | Young |
| 6,626,908 B2 | 9/2003 | Cooper et al. |
| 6,641,586 B2 | 11/2003 | Varieur |
| 6,652,526 B1 | 11/2003 | Arafiles |
| 6,660,004 B2 | 12/2003 | Barker et al. |
| 6,660,006 B2 | 12/2003 | Markworth et al. |
| 6,689,137 B2 | 2/2004 | Reed |
| 6,692,500 B2 | 2/2004 | Reed |
| 6,695,843 B2 | 2/2004 | Biedermann et al. |
| 6,702,817 B2 | 3/2004 | Beger et al. |
| 6,706,045 B2 | 3/2004 | Lin et al. |
| 6,716,214 B1 | 4/2004 | Jackson |
| 6,723,100 B2 | 4/2004 | Biedermann et al. |
| 6,730,092 B2 | 5/2004 | Songer |
| 6,736,820 B2 | 5/2004 | Biedermann et al. |
| 6,740,086 B2 | 5/2004 | Richelsoph |
| 6,755,829 B1 | 6/2004 | Bono et al. |
| 6,755,835 B2 | 6/2004 | Schultheiss et al. |
| 6,770,075 B2 | 8/2004 | Howland |
| 6,783,527 B2 | 8/2004 | Drewry et al. |
| 6,786,907 B2 | 9/2004 | Lange |
| 6,800,078 B2 | 10/2004 | Reed |
| 6,800,079 B2 | 10/2004 | Reed |
| 6,835,196 B2 | 12/2004 | Biedermann et al. |
| 6,837,889 B2 | 1/2005 | Shluzas |
| 6,843,791 B2 | 1/2005 | Serhan |
| 6,858,030 B2 | 2/2005 | Martin et al. |
| 6,858,031 B2 | 2/2005 | Morrison et al. |
| 6,869,432 B2 | 3/2005 | Schlapfer et al. |
| 6,869,433 B2 | 3/2005 | Glascott |
| 6,887,242 B2 | 5/2005 | Doubler et al. |
| 6,896,677 B1 | 5/2005 | Lin |
| 6,905,500 B2 | 6/2005 | Jeon et al. |
| 6,918,911 B2 | 7/2005 | Biedermann et al. |

(56) References Cited

U.S. PATENT DOCUMENTS

| | | |
|---|---|---|
| 6,951,561 B2 | 10/2005 | Warren et al. |
| 6,964,664 B2 | 11/2005 | Fried et al. |
| 6,964,666 B2 | 11/2005 | Jackson |
| 6,974,460 B2 | 12/2005 | Carbone et al. |
| 6,981,973 B2 | 1/2006 | McKinley |
| 7,018,379 B2 | 3/2006 | Drewry et al. |
| 7,022,122 B2 | 4/2006 | Amrein et al. |
| RE39,089 E | 5/2006 | Ralph et al. |
| 7,141,051 B2 | 11/2006 | Janowski et al. |
| 7,163,539 B2 | 1/2007 | Abdelgany et al. |
| 7,186,255 B2 | 3/2007 | Baynham et al. |
| 7,211,086 B2 | 5/2007 | Biedermann et al. |
| 7,223,268 B2 | 5/2007 | Biedermann |
| 7,250,052 B2 | 7/2007 | Landry et al. |
| 7,264,621 B2 | 9/2007 | Coates et al. |
| 7,303,562 B2 | 12/2007 | Cavagna et al. |
| 7,314,467 B2 | 1/2008 | Howland |
| 7,316,684 B1 | 1/2008 | Baccelli et al. |
| 7,322,979 B2 | 1/2008 | Crandall et al. |
| 7,335,202 B2 | 2/2008 | Matthis et al. |
| 7,377,923 B2 | 5/2008 | Purcell et al. |
| 7,445,627 B2 | 11/2008 | Hawkes et al. |
| 7,476,239 B2 | 1/2009 | Jackson |
| 7,530,992 B2 | 5/2009 | Biedermann et al. |
| 7,604,655 B2 | 10/2009 | Warnick |
| D603,503 S | 11/2009 | Kriska et al. |
| D603,504 S | 11/2009 | Kriska et al. |
| D603,505 S | 11/2009 | Kriska et al. |
| D603,506 S | 11/2009 | Kriska et al. |
| D603,507 S | 11/2009 | Kriska et al. |
| D603,508 S | 11/2009 | Kriska et al. |
| D603,509 S | 11/2009 | Kriska et al. |
| D603,510 S | 11/2009 | Kriska et al. |
| D603,511 S | 11/2009 | Kriska et al. |
| D603,961 S | 11/2009 | Kriska et al. |
| D603,962 S | 11/2009 | Kriska et al. |
| D603,963 S | 11/2009 | Kriska et al. |
| D603,964 S | 11/2009 | Kriska et al. |
| 7,625,394 B2 | 12/2009 | Molz, IV et al. |
| 7,635,380 B2 | 12/2009 | Zucherman et al. |
| 7,678,137 B2 | 3/2010 | Butler et al. |
| 7,691,129 B2 | 4/2010 | Felix |
| 7,691,132 B2 | 4/2010 | Landry et al. |
| 7,717,941 B2 | 5/2010 | Petit |
| 7,744,635 B2 | 6/2010 | Sweeny et al. |
| 7,766,944 B2 | 8/2010 | Metz-Stavenhagen |
| 7,776,040 B2 | 8/2010 | Markworth et al. |
| 7,780,706 B2 | 8/2010 | Marino et al. |
| 7,833,252 B2 | 11/2010 | Justis et al. |
| 7,875,065 B2 | 1/2011 | Jackson |
| 7,892,257 B2 | 2/2011 | Abdelgany |
| 7,914,558 B2 | 3/2011 | Landry et al. |
| 7,931,676 B2 | 4/2011 | Veldman et al. |
| 7,931,678 B2 | 4/2011 | Konieczynski et al. |
| 7,951,172 B2 | 5/2011 | Chao et al. |
| 8,002,806 B2 | 8/2011 | Justis |
| 8,012,186 B2 | 9/2011 | Pham et al. |
| 8,021,397 B2 | 9/2011 | Farris et al. |
| 8,038,701 B2 | 10/2011 | Rock et al. |
| 8,048,129 B2 | 11/2011 | Forton et al. |
| 8,075,594 B2 | 12/2011 | Purcell |
| 8,092,494 B2 | 1/2012 | Butler et al. |
| 8,097,020 B2 | 1/2012 | Markworth et al. |
| 8,100,946 B2 | 1/2012 | Strausbaugh et al. |
| 8,118,842 B2 | 2/2012 | Klyce et al. |
| 8,167,910 B2 | 5/2012 | Nilsson |
| 8,167,912 B2 | 5/2012 | Jacofsky et al. |
| 8,167,913 B2 | 5/2012 | Albert et al. |
| 8,221,472 B2 | 7/2012 | Peterson et al. |
| 8,337,530 B2 | 12/2012 | Hestad et al. |
| 8,398,682 B2 | 3/2013 | Jackson et al. |
| 8,449,577 B2 | 5/2013 | Kloss et al. |
| 8,628,558 B2 | 1/2014 | Harvey et al. |
| 8,632,571 B2 | 1/2014 | Kraus |
| 9,084,634 B1 | 7/2015 | Lab et al. |
| 9,649,142 B2 | 5/2017 | Doubler |
| 9,707,014 B1 | 7/2017 | Lab et al. |
| 10,206,717 B1 | 2/2019 | Lab et al. |
| 10,603,083 B1 | 3/2020 | Gladieux et al. |
| 2001/0001119 A1 | 5/2001 | Lombardo |
| 2002/0010467 A1 | 1/2002 | Cooper et al. |
| 2002/0022842 A1 | 2/2002 | Horvath et al. |
| 2002/0026193 A1 | 2/2002 | Barker et al. |
| 2002/0035366 A1 | 3/2002 | Walder et al. |
| 2002/0058942 A1 | 5/2002 | Biedermann et al. |
| 2002/0082602 A1 | 6/2002 | Biedermann et al. |
| 2002/0091386 A1 | 7/2002 | Martin et al. |
| 2002/0120272 A1 | 8/2002 | Yuan |
| 2002/0133154 A1 | 9/2002 | Saint Martin |
| 2002/0138076 A1 | 9/2002 | Biedermann et al. |
| 2002/0143341 A1 | 10/2002 | Biedermann et al. |
| 2002/0151900 A1 | 10/2002 | Glascott |
| 2002/0183748 A1 | 12/2002 | Martin et al. |
| 2003/0004512 A1 | 1/2003 | Farris et al. |
| 2003/0023243 A1 | 1/2003 | Biedermann et al. |
| 2003/0032957 A1 | 2/2003 | McKinley |
| 2003/0073996 A1 | 4/2003 | Doubler et al. |
| 2003/0073997 A1 | 4/2003 | Doubler et al. |
| 2003/0083657 A1 | 5/2003 | Drewry et al. |
| 2003/0100896 A1 | 5/2003 | Biedermann et al. |
| 2003/0100904 A1 | 5/2003 | Biedermann |
| 2003/0125741 A1 | 7/2003 | Biedermann et al. |
| 2003/0149431 A1 | 8/2003 | Varieur |
| 2003/0158552 A1 | 8/2003 | Jeon et al. |
| 2003/0187439 A1 | 10/2003 | Biedermann et al. |
| 2003/0187442 A1 | 10/2003 | Richelsoph et al. |
| 2003/0199873 A1 | 10/2003 | Richelsoph |
| 2004/0030337 A1 | 2/2004 | Alleyne et al. |
| 2004/0097933 A1 | 5/2004 | Lourdel et al. |
| 2004/0102781 A1 | 5/2004 | Jeon |
| 2004/0116929 A1 | 6/2004 | Barker |
| 2004/0138660 A1 | 7/2004 | Serhan |
| 2004/0138662 A1 | 7/2004 | Landry et al. |
| 2004/0143265 A1 | 7/2004 | Landry et al. |
| 2004/0153077 A1 | 8/2004 | Biedermann et al. |
| 2004/0158247 A1 | 8/2004 | Sitiso et al. |
| 2004/0172022 A1 | 9/2004 | Landry et al. |
| 2004/0172025 A1 | 9/2004 | Drewry et al. |
| 2004/0181224 A1 | 9/2004 | Biedermann et al. |
| 2004/0186473 A1 | 9/2004 | Cournoyer et al. |
| 2004/0186474 A1 | 9/2004 | Matthis et al. |
| 2004/0193160 A1 | 9/2004 | Richelsoph |
| 2004/0225289 A1 | 11/2004 | Biedermann et al. |
| 2004/0230192 A1 | 11/2004 | Graf |
| 2004/0236330 A1 | 11/2004 | Purcell et al. |
| 2004/0243126 A1 | 12/2004 | Carbone et al. |
| 2004/0249378 A1 | 12/2004 | Saint Martin et al. |
| 2004/0249380 A1 | 12/2004 | Glascott |
| 2004/0260283 A1 | 12/2004 | Wu et al. |
| 2004/0260284 A1 | 12/2004 | Parker |
| 2004/0267264 A1 | 12/2004 | Konieczynski et al. |
| 2005/0010218 A1 | 1/2005 | Dalton |
| 2005/0010219 A1 | 1/2005 | Dalton |
| 2005/0033296 A1 | 2/2005 | Bono et al. |
| 2005/0033298 A1 | 2/2005 | Hawkes et al. |
| 2005/0038430 A1 | 2/2005 | McKinley |
| 2005/0049588 A1 | 3/2005 | Jackson |
| 2005/0049589 A1 | 3/2005 | Jackson |
| 2005/0055026 A1 | 3/2005 | Biedermann et al. |
| 2005/0070899 A1 | 3/2005 | Doubler et al. |
| 2005/0070901 A1 | 3/2005 | David |
| 2005/0080415 A1 | 4/2005 | Keyer et al. |
| 2005/0080420 A1 | 4/2005 | Farris et al. |
| 2005/0085812 A1 | 4/2005 | Sherman et al. |
| 2005/0119658 A1 | 6/2005 | Ralph et al. |
| 2005/0131410 A1 | 6/2005 | Lin |
| 2005/0137594 A1 | 6/2005 | Doubler et al. |
| 2005/0154389 A1 | 7/2005 | Selover et al. |
| 2005/0154391 A1 | 7/2005 | Doherty et al. |
| 2005/0171542 A1 | 8/2005 | Biedermann et al. |
| 2005/0177154 A1 | 8/2005 | Moumene et al. |
| 2005/0187548 A1 | 8/2005 | Butler et al. |
| 2005/0187555 A1 | 8/2005 | Biedermann |
| 2005/0192571 A1 | 9/2005 | Abdelgany |

(56) References Cited

U.S. PATENT DOCUMENTS

| | | |
|---|---|---|
| 2005/0192573 A1 | 9/2005 | Abdelgany et al. |
| 2005/0192580 A1 | 9/2005 | Dalton |
| 2005/0192589 A1 | 9/2005 | Raymond et al. |
| 2005/0203515 A1 | 9/2005 | Doherty et al. |
| 2005/0203516 A1 | 9/2005 | Biedermann et al. |
| 2005/0216003 A1 | 9/2005 | Biedermann et al. |
| 2005/0228379 A1 | 10/2005 | Jackson |
| 2005/0228382 A1 | 10/2005 | Richelsoph |
| 2005/0240180 A1 | 10/2005 | Vienney et al. |
| 2005/0251139 A1 | 11/2005 | Roh |
| 2005/0261687 A1 | 11/2005 | Garamszegi et al. |
| 2005/0267472 A1 | 12/2005 | Biedermann et al. |
| 2005/0277923 A1 | 12/2005 | Sweeney |
| 2005/0277928 A1 | 12/2005 | Boschert |
| 2005/0277931 A1 | 12/2005 | Sweeney et al. |
| 2005/0283157 A1 | 12/2005 | Coates et al. |
| 2005/0288671 A1 | 12/2005 | Yuan |
| 2006/0036242 A1 | 2/2006 | Nilsson et al. |
| 2006/0036244 A1 | 2/2006 | Spitler et al. |
| 2006/0036252 A1 | 2/2006 | Baynham et al. |
| 2006/0036260 A1 | 2/2006 | Runco et al. |
| 2006/0052783 A1 | 3/2006 | Dant et al. |
| 2006/0052784 A1 | 3/2006 | Dant et al. |
| 2006/0058788 A1 | 3/2006 | Hammer et al. |
| 2006/0074419 A1 | 4/2006 | Taylor et al. |
| 2006/0084979 A1 | 4/2006 | Jackson |
| 2006/0084980 A1 | 4/2006 | Melkent et al. |
| 2006/0084981 A1 | 4/2006 | Shluzas |
| 2006/0084993 A1 | 4/2006 | Landry et al. |
| 2006/0129149 A1 | 6/2006 | Iott et al. |
| 2006/0142761 A1 | 6/2006 | Landry et al. |
| 2006/0149245 A1 | 7/2006 | Sweeney |
| 2006/0200128 A1 | 9/2006 | Mueller |
| 2006/0200131 A1* | 9/2006 | Chao ............... A61B 17/7038 606/278 |
| 2006/0235389 A1 | 10/2006 | Albert et al. |
| 2007/0055235 A1 | 3/2007 | Janowski et al. |
| 2007/0090238 A1 | 4/2007 | Justis |
| 2007/0118123 A1 | 5/2007 | Strausbaugh et al. |
| 2008/0015576 A1* | 1/2008 | Whipple ............ A61B 17/7037 606/60 |
| 2008/0021473 A1 | 1/2008 | Butler et al. |
| 2008/0097441 A1 | 4/2008 | Hayes et al. |
| 2008/0132953 A1 | 6/2008 | Carbone et al. |
| 2008/0147129 A1* | 6/2008 | Biedermann ...... A61B 17/7032 606/308 |
| 2008/0161859 A1 | 7/2008 | Nilsson |
| 2008/0177260 A1 | 7/2008 | McKinley |
| 2008/0183223 A1 | 7/2008 | Jeon et al. |
| 2008/0195159 A1* | 8/2008 | Kloss ............... A61B 17/7037 606/305 |
| 2008/0243189 A1 | 10/2008 | Purcell et al. |
| 2008/0262556 A1 | 10/2008 | Jacofsky et al. |
| 2008/0312655 A1 | 12/2008 | Kirschman et al. |
| 2009/0062914 A1 | 3/2009 | Marino |
| 2009/0105716 A1 | 4/2009 | Barrus |
| 2009/0105770 A1 | 4/2009 | Berrevoets et al. |
| 2009/0118772 A1 | 5/2009 | Diederich et al. |
| 2010/0063545 A1 | 3/2010 | Richelsoph |
| 2010/0087873 A1 | 4/2010 | Null et al. |
| 2010/0125302 A1 | 5/2010 | Hammill et al. |
| 2010/0204735 A1 | 8/2010 | Gephart et al. |
| 2010/0249837 A1 | 9/2010 | Seme et al. |
| 2011/0054536 A1 | 3/2011 | Elsebaie et al. |
| 2011/0098747 A1 | 4/2011 | Donner et al. |
| 2011/0106174 A1 | 5/2011 | Rezach |
| 2011/0112578 A1* | 5/2011 | Keiser ............... A61B 17/7037 606/264 |
| 2011/0178558 A1 | 7/2011 | Barry |
| 2011/0178559 A1 | 7/2011 | Barry |
| 2011/0196431 A1 | 8/2011 | Chao et al. |
| 2011/0257690 A1 | 10/2011 | Rezach |
| 2012/0109218 A1 | 5/2012 | Farris |
| 2013/0090693 A1 | 4/2013 | Strausbaugh et al. |
| 2013/0110178 A1 | 5/2013 | Biedermann |
| 2014/0188171 A1 | 7/2014 | Huang |

OTHER PUBLICATIONS

PCT/US2004/010319 International Search Report dated Oct. 14, 2004, p. 1.

PCT/US2004/010319 Written Opinion of the International Search Authority dated Oct. 14, 2004, pp. 1-3.

U.S. Appl. No. 16/834,556, filed Mar. 30, 2020 titled Apparatus and Method for Limiting a Range of Angular Positions of a Screw.

* cited by examiner

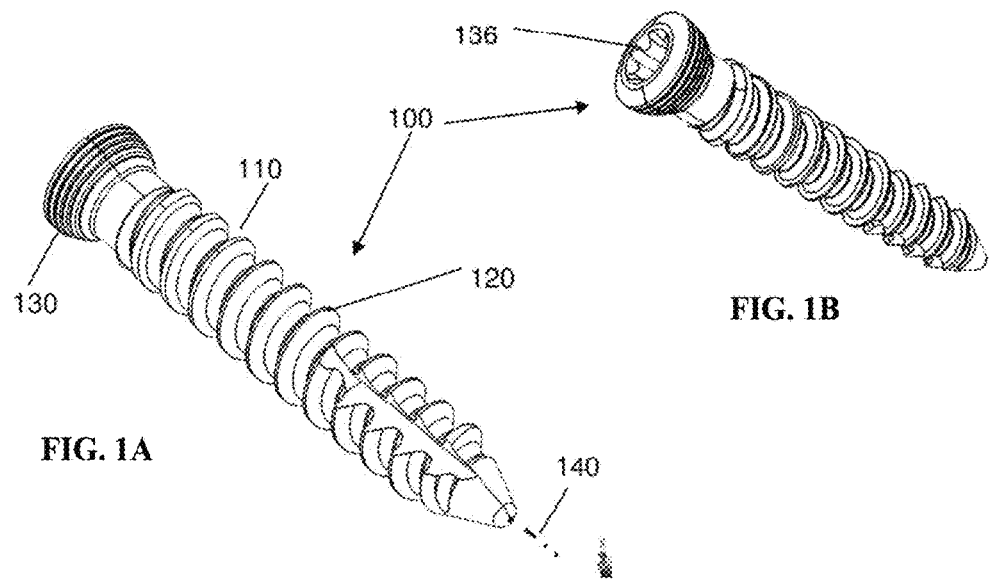
FIG. 1A
FIG. 1B
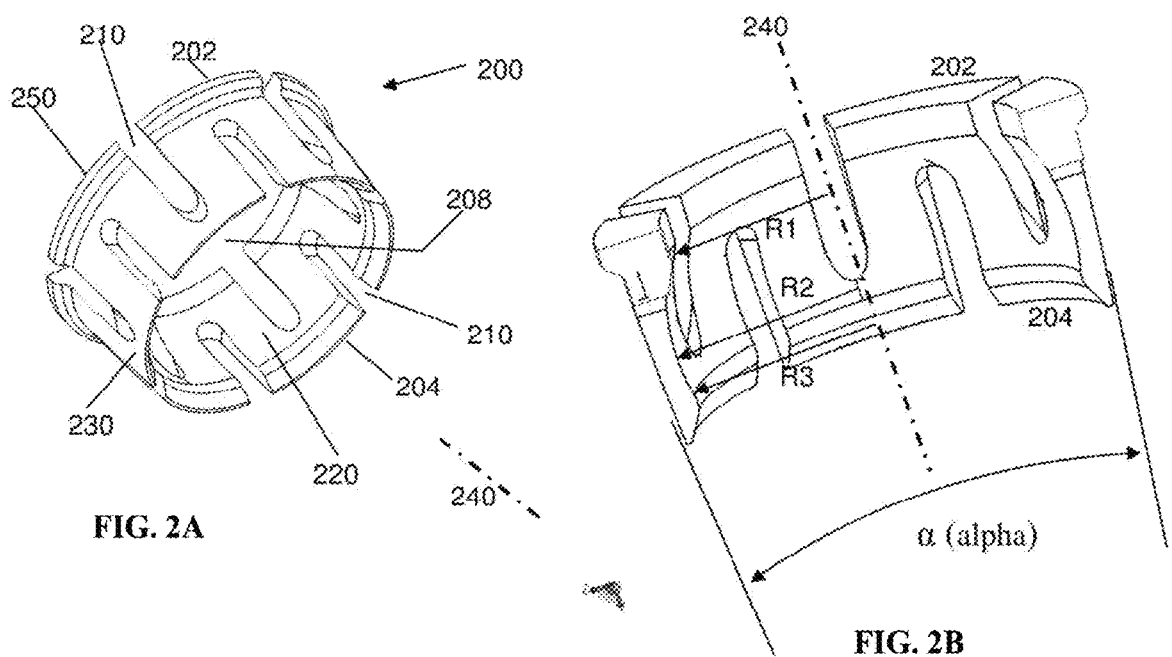
FIG. 2A
FIG. 2B

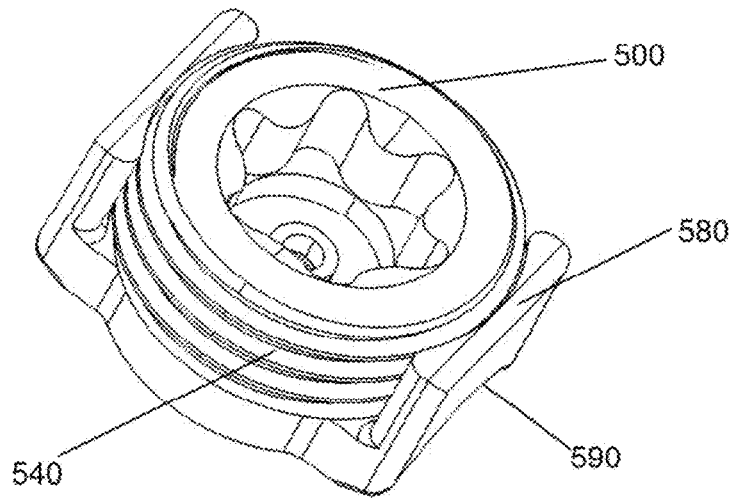
FIG. 4
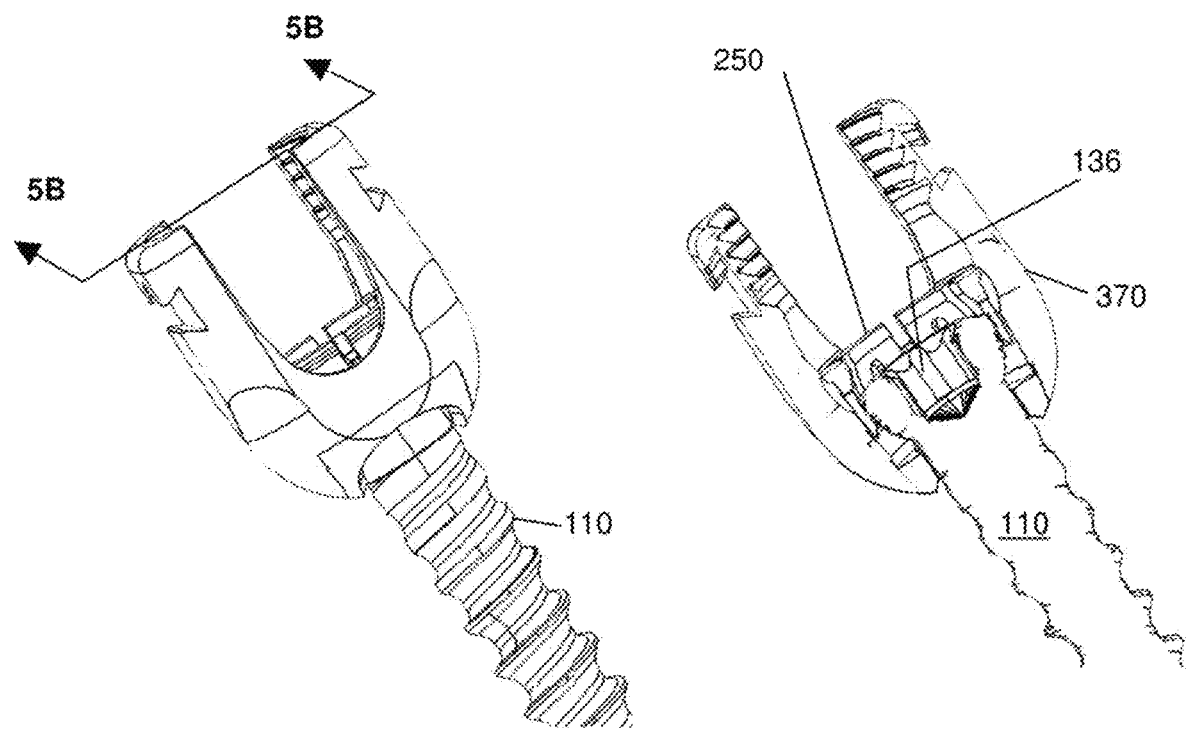
FIG. 5A
FIG. 5B

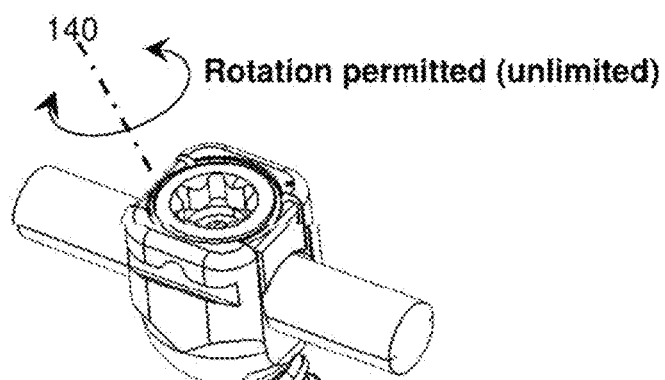
FIG. 6A
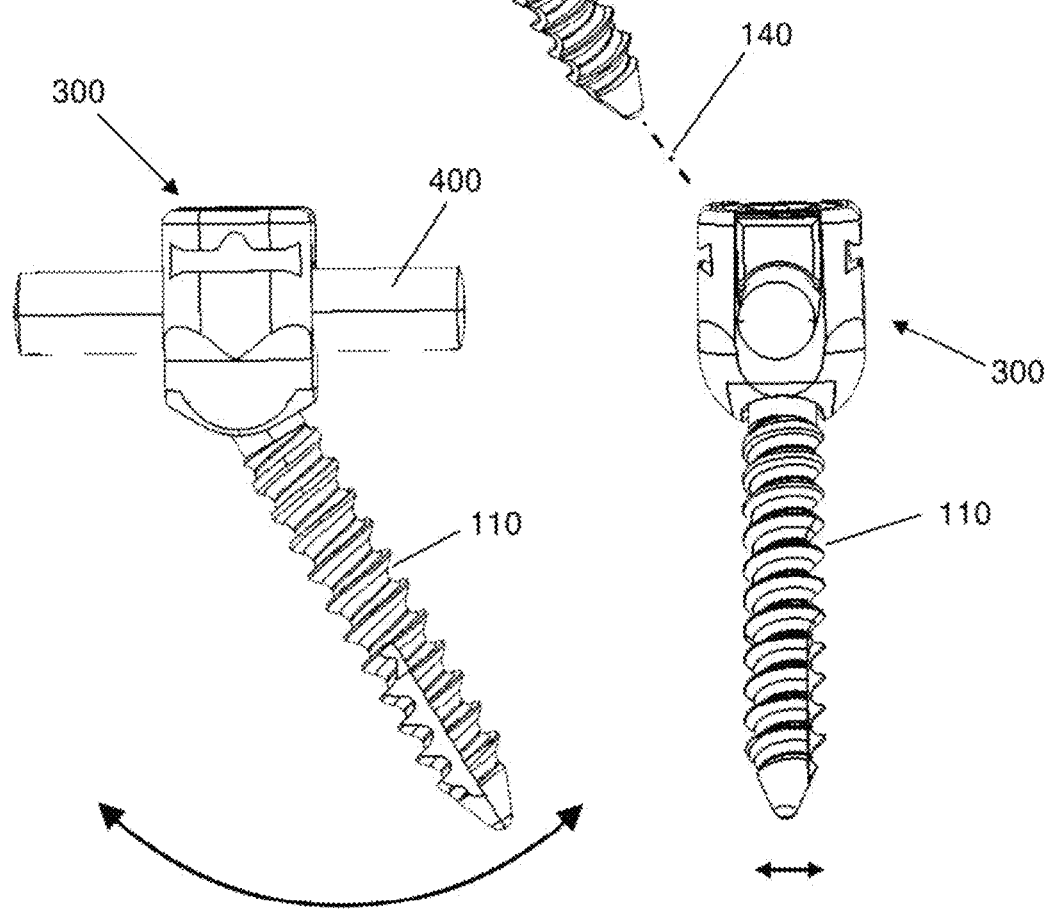
Angulation permitted (within limits)
FIG. 6B
Little or no angulation permitted
FIG. 6C

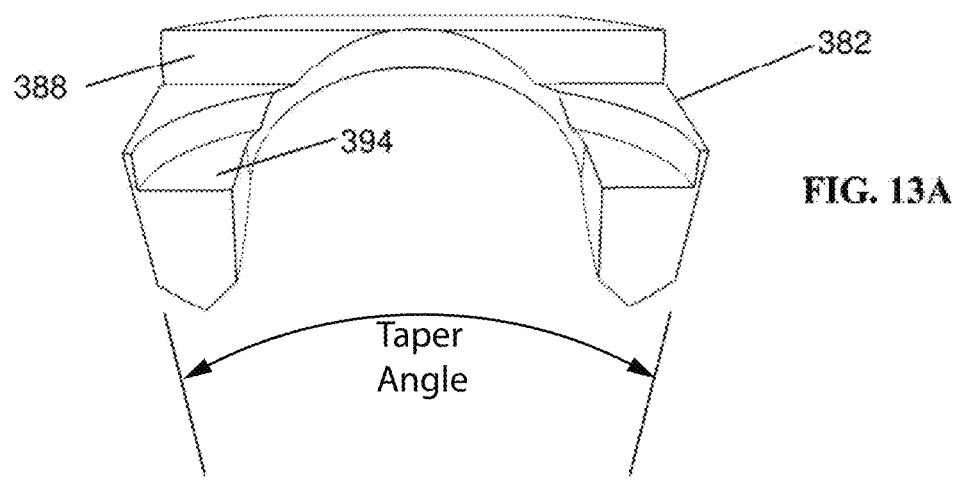
FIG. 13A
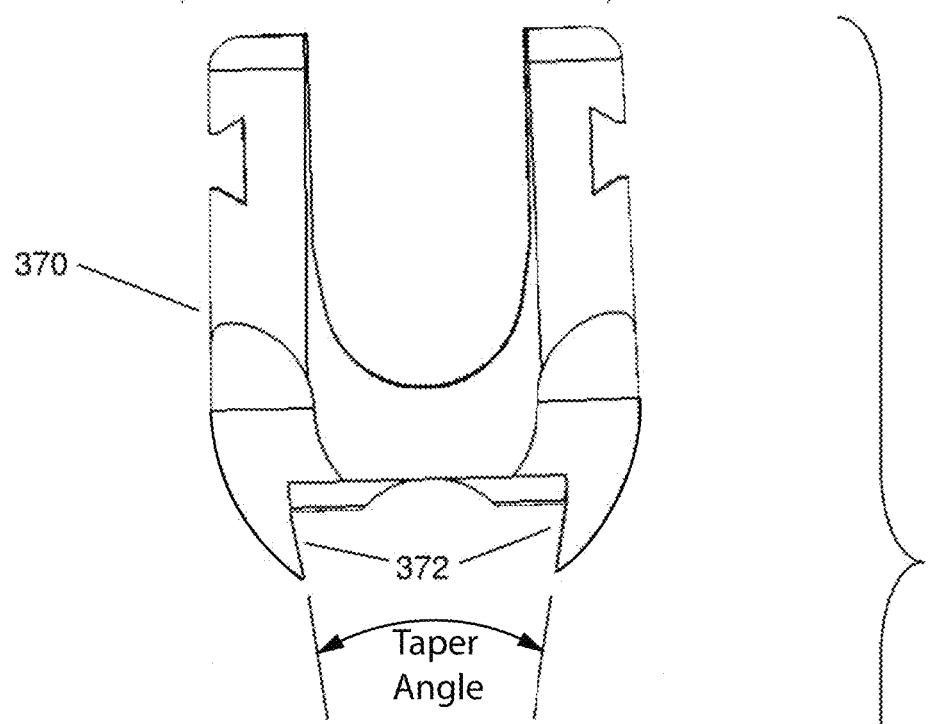
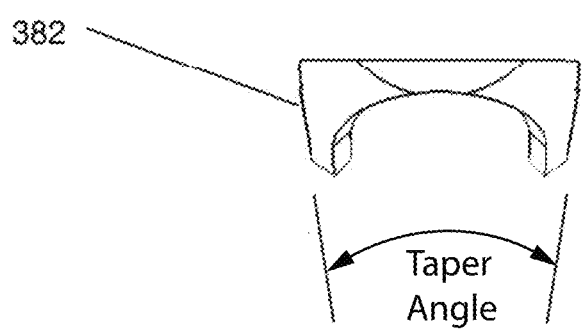
FIG. 13B

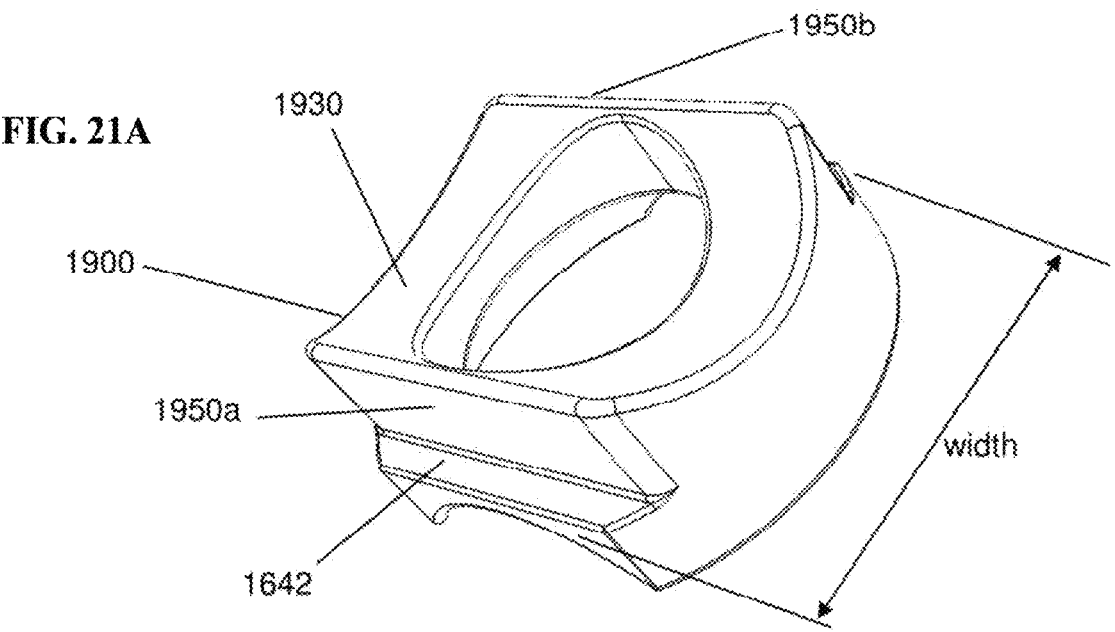
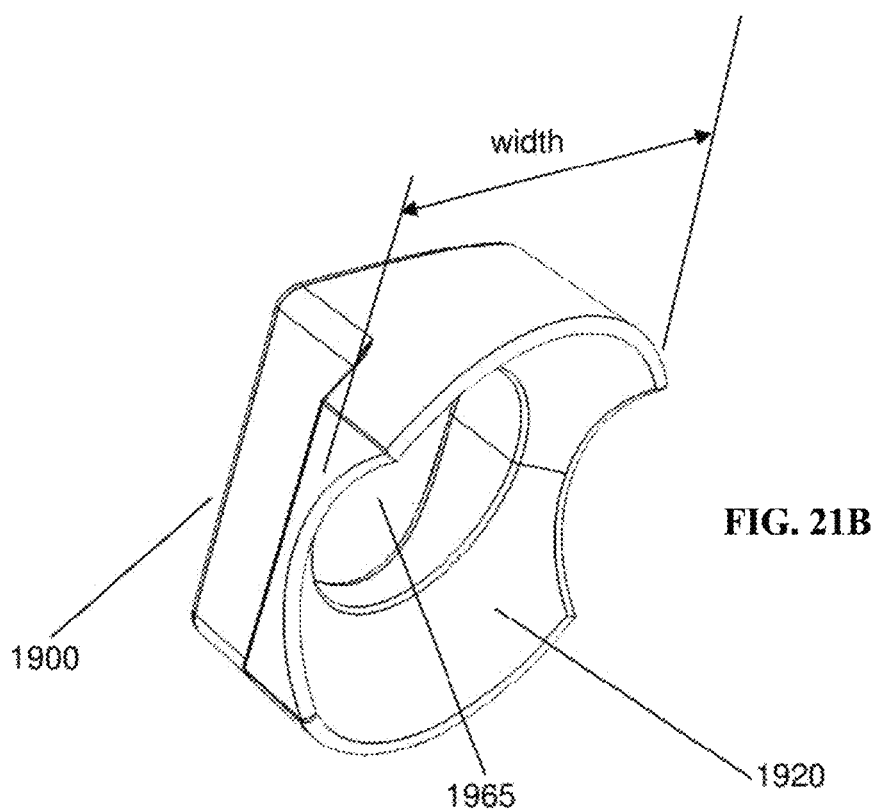

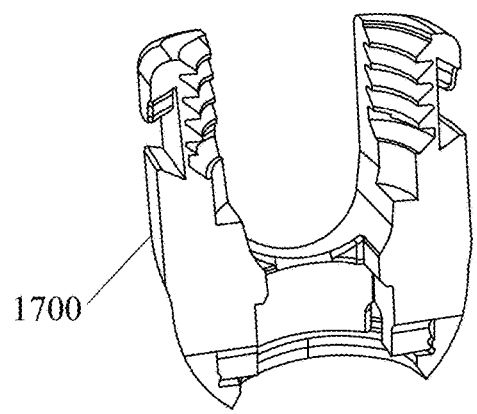
FIG. 25A
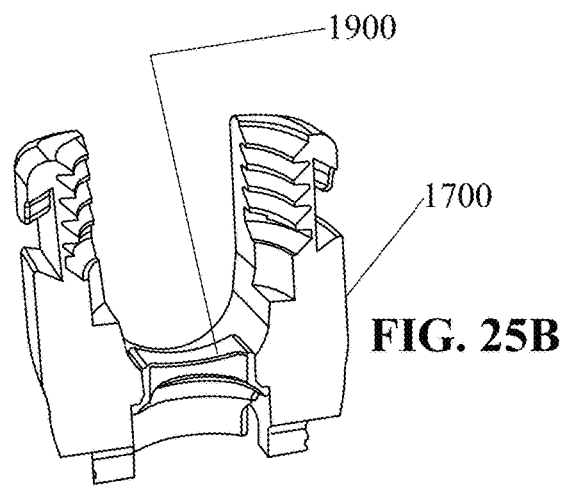
FIG. 25B
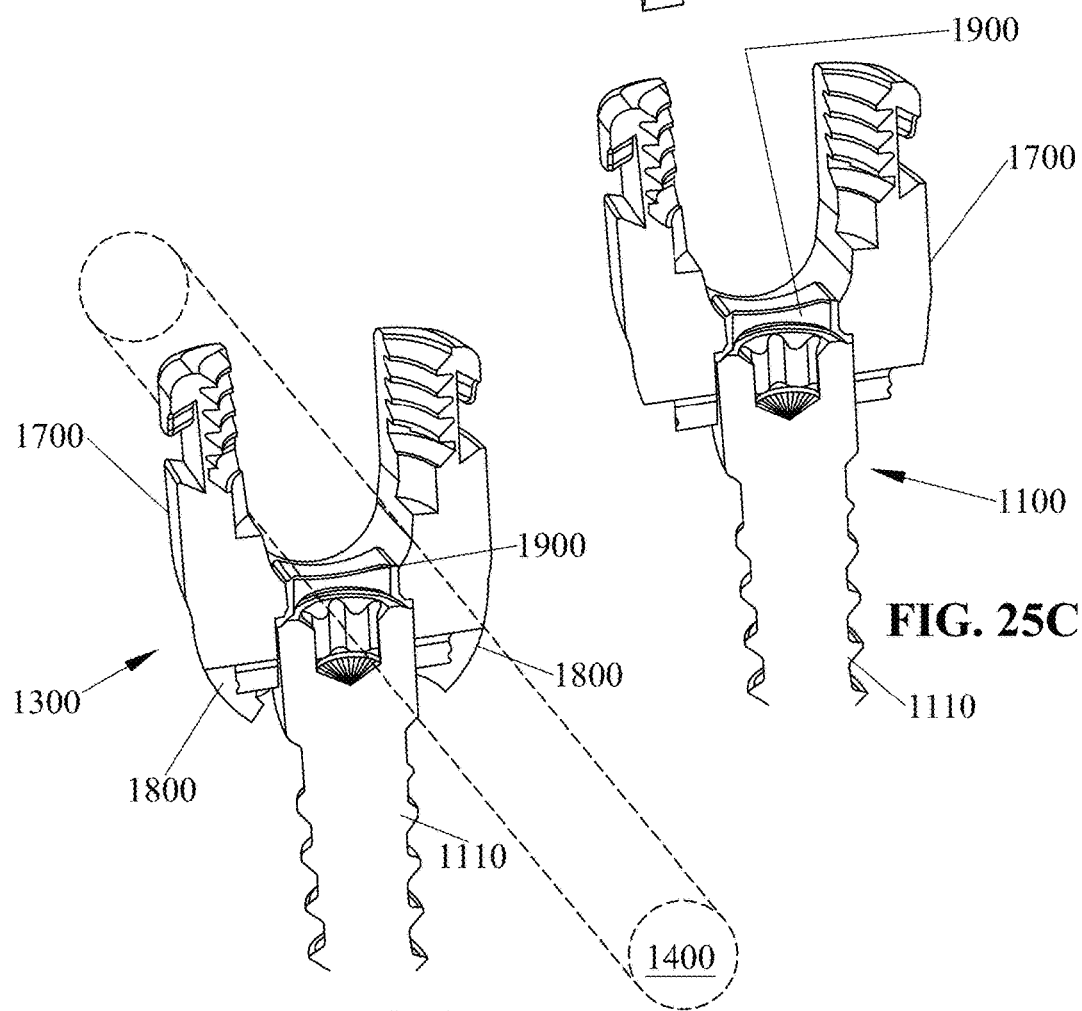
FIG. 25C
FIG. 25D

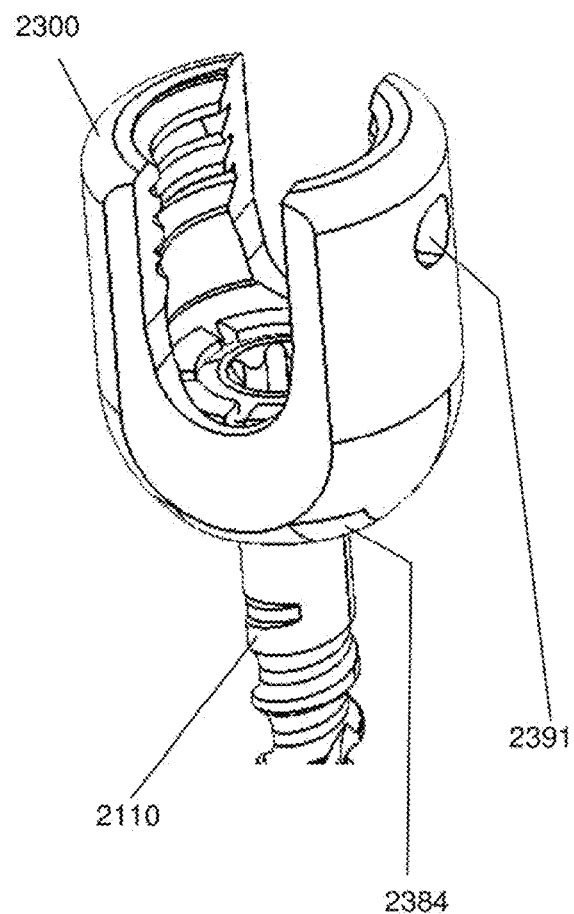
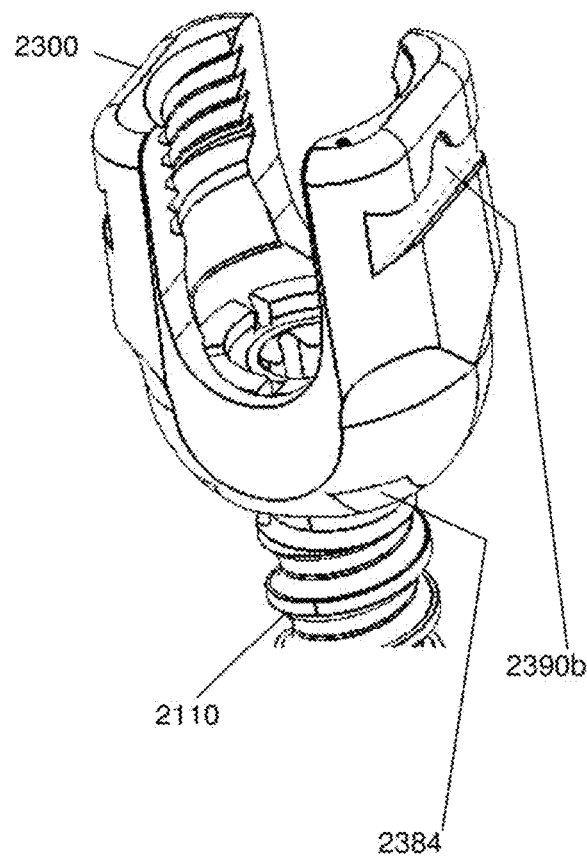
FIG. 29A
FIG. 29B

APPARATUS AND METHOD FOR LIMITING A RANGE OF ANGULAR POSITIONS OF A SCREW

CROSS-REFERENCE TO RELATED APPLICATIONS

This application is a divisional patent application of and claims priority and benefit under 35 U.S.C. § 121 to U.S. patent application Ser. No. 15/449,460, filed on Mar. 3, 2017, now U.S. Pat. No. 10,206,717, which claims priority to U.S. patent application Ser. No. 14/797,702 filed on Jul. 13, 2015, now U.S. Pat. No. 9,707,014, which claims priority to U.S. patent application Ser. No. 13/180,332, filed on Jul. 11, 2011, now U.S. Pat. No. 9,084,634, which claims priority to U.S. Provisional App. No. 61/362,993, filed on Jul. 9, 2010. This application is also related to U.S. patent application Ser. Nos. 12/117,609; 12/117,615; and Ser. No. 12/117,613. The entire contents of the aforementioned applications are herein incorporated by reference in their entirety.

TECHNICAL FIELD

Embodiments of the invention pertain to spinal surgery.

BACKGROUND

Spinal surgery frequently uses polyaxial pedicle screws that may allow angulation in various degrees of freedom between the movable screw head and the screw itself. Such screws may have a spherical screw head captured somewhere within the movable head. A uniplanar screw may be provided that allows angulation in one plane but prevents or limits angulation in another plane mutually perpendicular to the first plane.

SUMMARY

In an embodiment, there may be provided a spinal screw apparatus in which the movable head has a bottom opening shaped so as to allow more angulation in a first angulation plane than in a second angulation plane that is perpendicular to the first angulation plane.

In another embodiment, there may be provided a spinal screw apparatus in which the movable head possesses a proximal portion and at least one distal portion joined to the proximal portion, and the distal portion has a mechanical interlock with the proximal portion.

In another embodiment, there may be provided a spinal screw apparatus in which the movable head possesses a proximal portion and two distal portions each joinable to the proximal portion.

Yet another embodiment may provide a spinal screw apparatus in which the screw head and movable head each have at least one flat surface, and the corresponding flat surfaces face directly toward each other.

In another embodiment, a spinal screw apparatus is provided with a screw, a movable head, and a collet. The screw has a shaft or shank and a screw head. The screw head may be fixedly attached to the shaft or shank such that it is connected as a separate piece or may possibly be integrated with the shaft or shank to be formed as a single piece. The movable head may have a concave interior larger than the screw head. The collet may be interposed between the screw head and the concave interior of the movable head. The movable head has a bottom opening shaped so as to allow more angulation around a first rotational direction than around a second rotational direction that is perpendicular to the first rotational direction.

Another embodiment provides a moveable head for a spinal screw apparatus. The movable head may be provided with a body having an opening therethrough. The opening may have an opening longitudinal axis and a proximal end and a distal end. The body may also have an internal surface defining an internal cavity having a distal end opening perimeter. The body may also have a proximal component and at least one distal component joined to the proximal component. The distal component may define at least a portion of the distal end opening perimeter. The distal component may have a mechanical interlock with the body.

Another embodiment provides a moveable head for a spinal screw apparatus. The movable head may be provided with a body having an opening therethrough. The opening may have an opening longitudinal axis and a proximal end and a distal end. The body may also have an internal surface defining an internal cavity having a distal end opening perimeter. The body may also have a proximal component and at least one distal component joined to the proximal component. The distal component may define at least a portion of the distal end opening perimeter. The distal component may have a first sub-motion-limiter that may be joinable to the proximal component and a second sub-motion-limiter that may also be joinable to the proximal component.

Yet another embodiment provides a spinal screw apparatus that has a screw and movable head. The screw may have a head and a shaft having a shaft axis. The screw head may be fixedly attached to the shaft such that it is connected as a separate piece or may possibly be integrated with the shaft to be formed as a single piece. The screw head may be provided with a portion of a sphere and may also have at least one flat external surface defining a plane substantially parallel to the shaft axis. The movable head may capture the screw head. The movable head may be configured to have a concave interior suitable to receive the screw head with the interior having a flat interior surface. The flat interior surface may directly face the flat external surface.

In a disclosed embodiment, there may be provided a screw apparatus having a movable head that has a groove or pair of grooves and receives a motion limiter or a pair of motion limiters. One of the motion limiters may be entirely to one side of the plane of a mid-plane of the movable head that contains an axis of a U-trough and a spinal rod, and the other of the motion limiters may be entirely to the other side of the mid-plane.

In yet another embodiment, there may be provided a screw apparatus that allows motion of the screw shaft relative to the movable head such that the motion is bounded by a shape that comprises a straight line segment and a curved segment.

In yet another embodiment, there may be provided a collet that has slots on a rod-contacting surface thereof, such that the slots are oriented in a non-radial direction.

BRIEF DESCRIPTION OF THE ILLUSTRATIONS

Embodiments are further described in the following illustrations.

FIGS. 1A and 1B are various three-dimensional perspective views of a screw used in an embodiment.

FIG. 2A is a three-dimensional perspective view of a collet used in an embodiment, and FIG. 2B is a cross-sectional view of the embodiment shown in FIG. 2A.

FIG. 4 is a three-dimensional perspective view of a set screw and saddle, as used in an embodiment.

FIG. 5A is a three-dimensional perspective view of a screw assembly.

FIG. 5B is a cross-section of the embodiment shown in FIG. 5A.

FIG. 6A is a three-dimensional perspective view of a screw assembly illustrating certain features regarding rotation and angulation of the screw with respect to the movable head.

FIG. 6B is a side view of the embodiment shown in FIG. 6A.

FIG. 6C is a side view of the embodiment shown in FIG. 6A.

FIG. 13A is a perspective view of a sub-motion-limiter.

FIG. 13B is a perspective view of a sub-motion-limiter and also a proximal portion, illustrating respective taper angles.

Figure 19A:
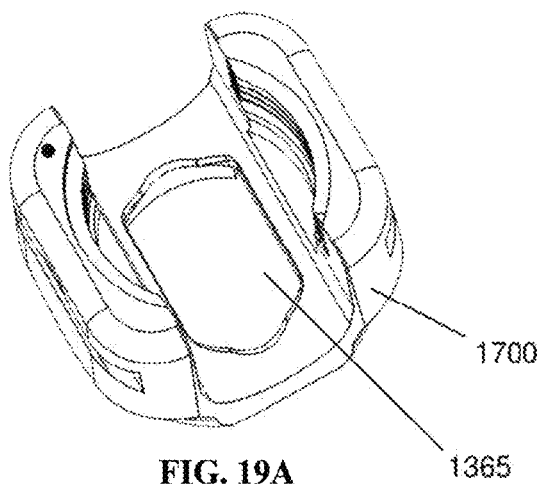
Figure 19B:
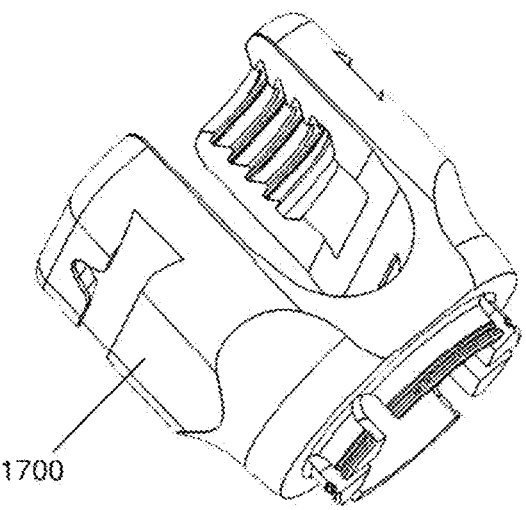
Figure 19C:
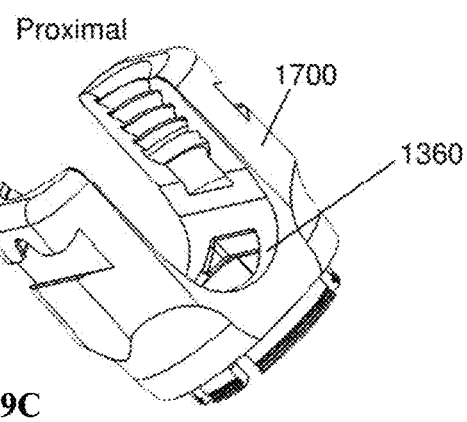

FIGS. 19A, 19B, and 19C are three-dimensional perspective views of the proximal portion of a movable head of an embodiment, each from a different vantage point.

Figure 19D:
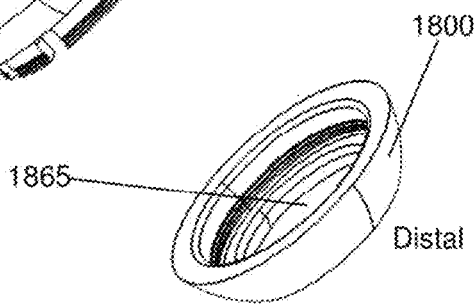

FIG. 19D is a three-dimensional perspective view of the distal portion of the movable head, suitable to connect to the proximal portion of the movable head shown in FIG. 19C.

Figure 20:
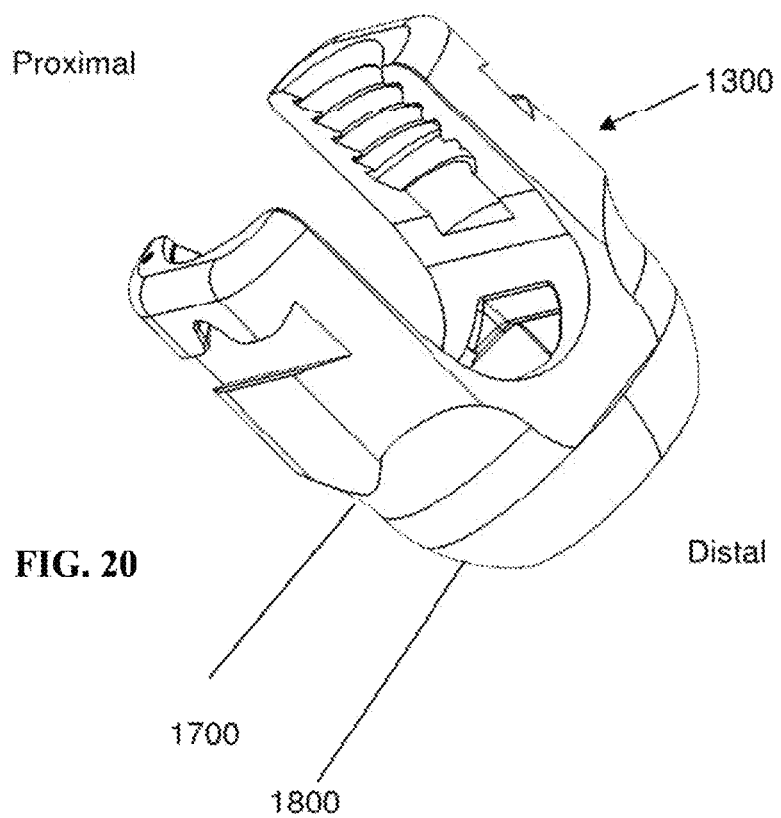

FIG. 20 is a three-dimensional perspective view showing the movable head shown in FIG. 19B and the bottom cap shown in FIG. 19C joined together.

FIGS. 21A and 21B are three-dimensional perspective views of a top-cap piece.

Figure 22A:
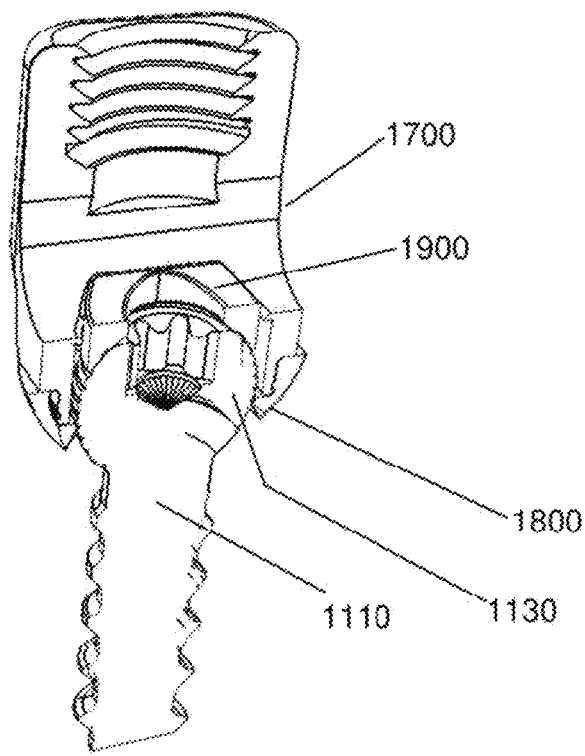

FIG. 22A is a three-dimensional cross-sectional view of an assembly of a disclosed embodiment.

Figure 22B:
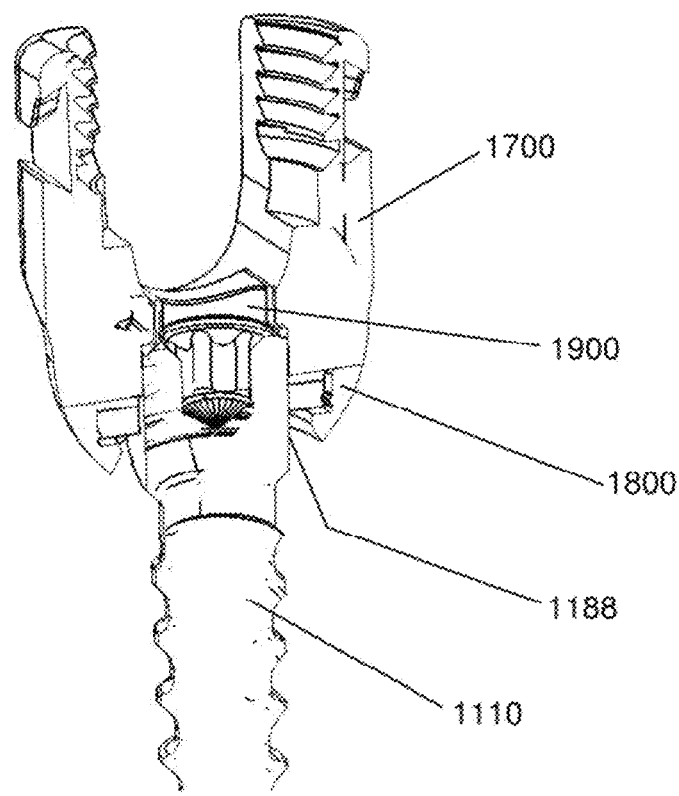

FIG. 22B is a three-dimensional cross-sectional view of the assembly shown in FIG. 22A from a different perspective.

Figure 23:
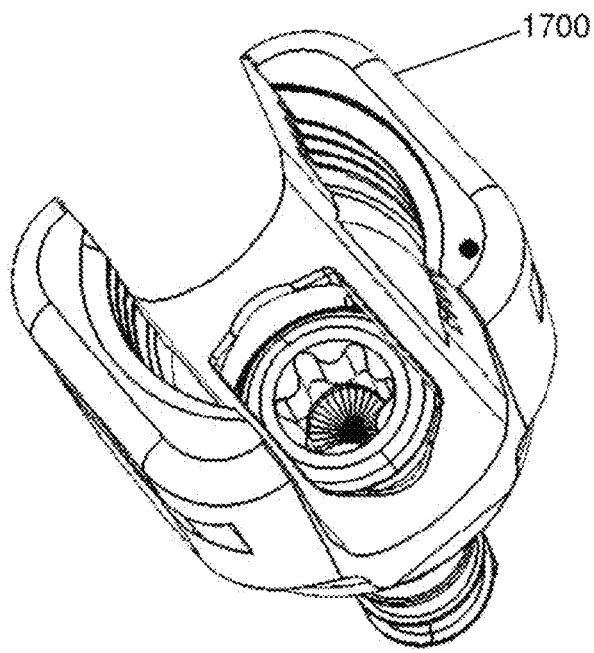

FIG. 23 is a three-dimensional perspective view showing only the movable head and the screw head.

Figure 24:
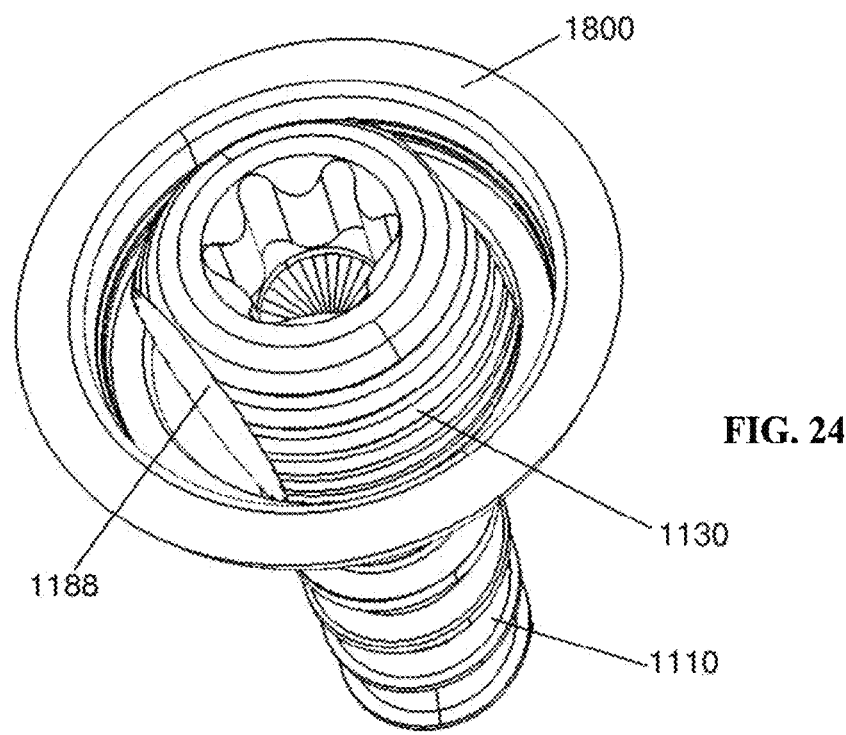

FIG. 24 is a three-dimensional perspective view showing only the screw head and the movable head distal portion.

FIGS. 25A-25D are three-dimensional perspective cross-sectional views of the apparatus in sequential stages of assembly.

Figure 26:
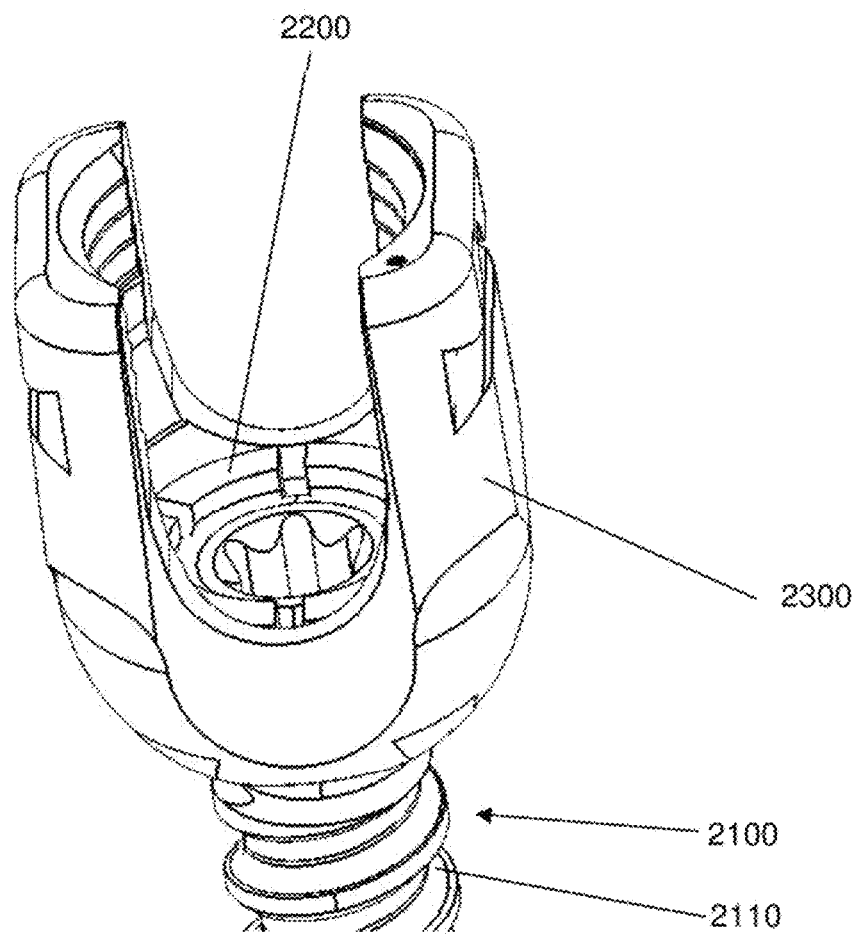

FIG. 26 is a three-dimensional perspective view of an embodiment of a screw.

Figure 27A:
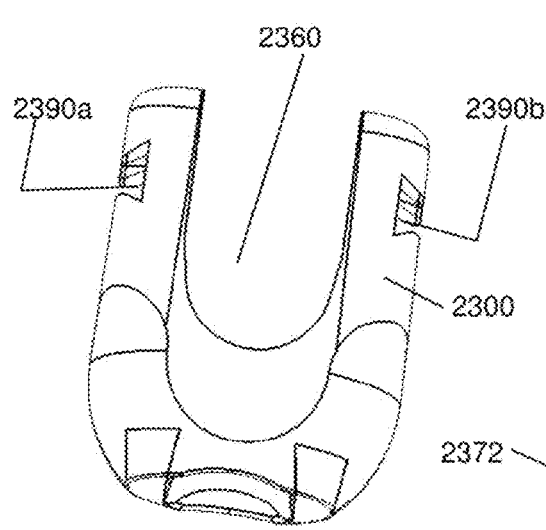

FIG. 27A is a perspective view of the movable head of the embodiment shown in FIG. 26.

Figure 27B:
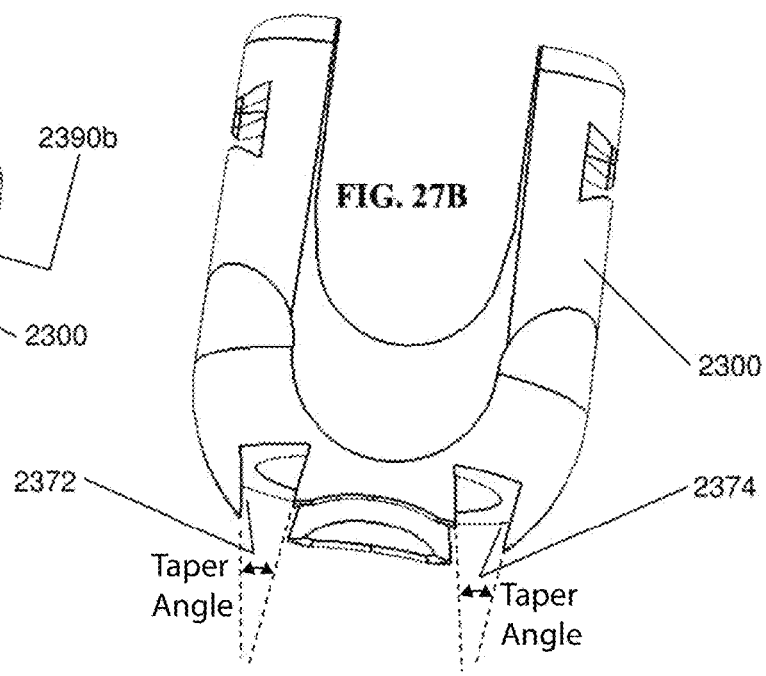

FIG. 27B shows the embodiment of FIG. 27A with the two motion limiters omitted for clarity.

Figure 27C:
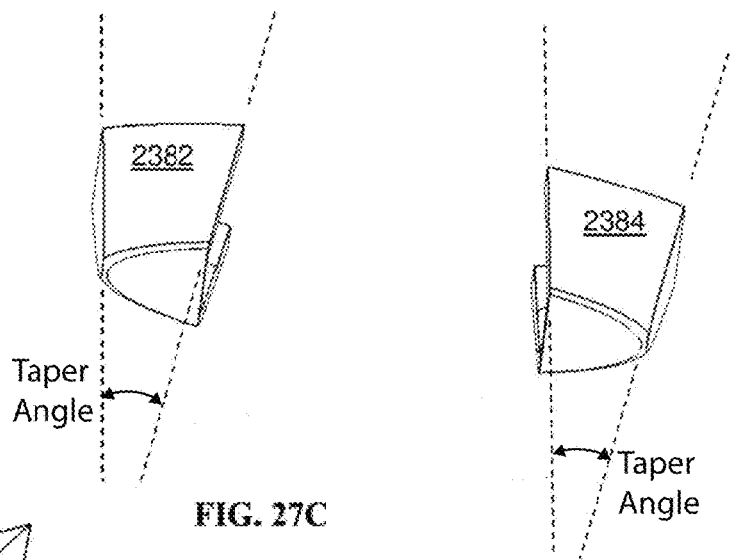

FIG. 27C shows the embodiment of FIG. 27A with the movable head omitted for clarity.

Figure 27D:
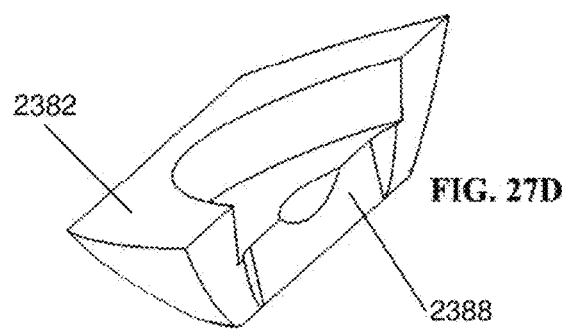

FIG. 27D is a perspective view of an embodiment of a motion limiter.

Figure 27E:
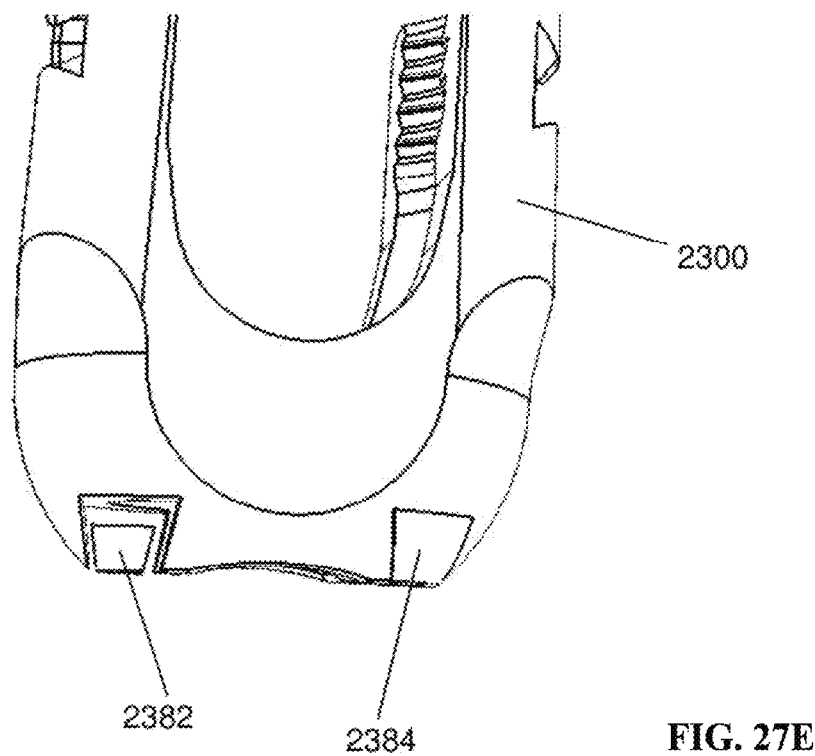
Figure 27F:
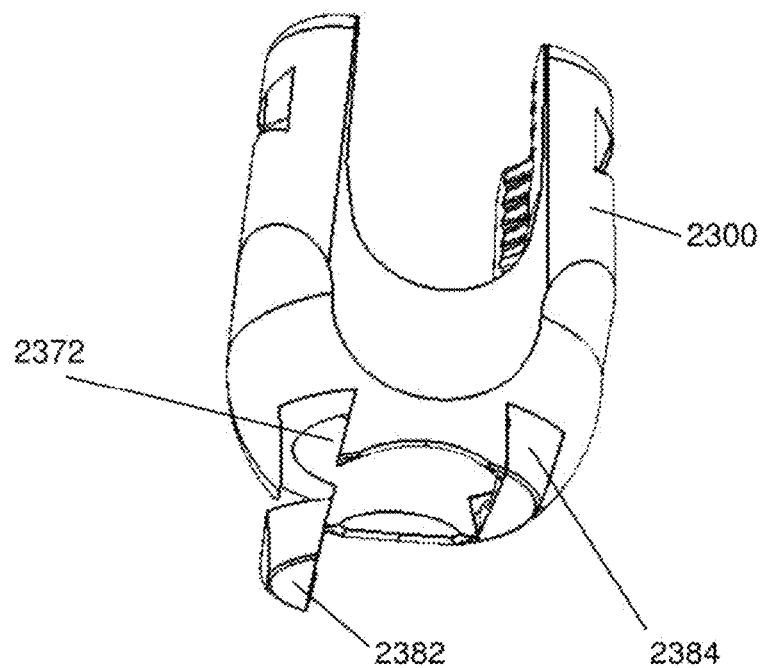

FIGS. 27E and 27F are perspective views of one embodiment of a motion limiter being inserted into an embodiment of a movable head, while the other motion limiter is already in place in the movable head.

Figure 28:
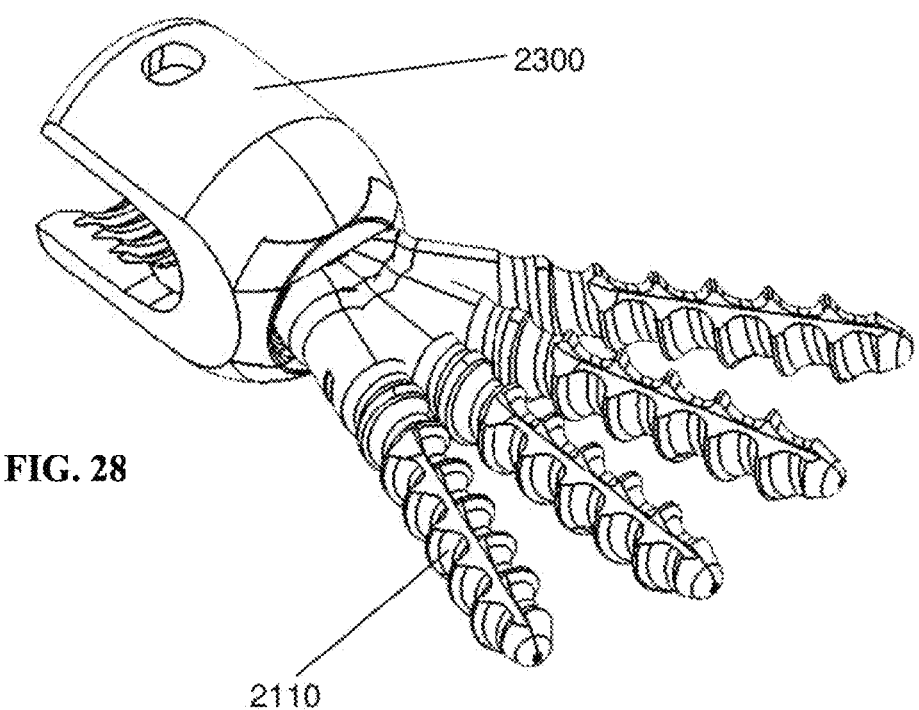

FIG. 28 is a composite view of the embodiment of a screw shown in FIG. 26 showing multiple possible positions of the screw shaft relative to the movable head.

FIG. 29A is a three-dimensional perspective view of a screw with a first design of certain external features of the movable head.

FIG. 29B is a three-dimensional perspective view of a screw with a second design of certain external features of the movable head.

Figure 30A:
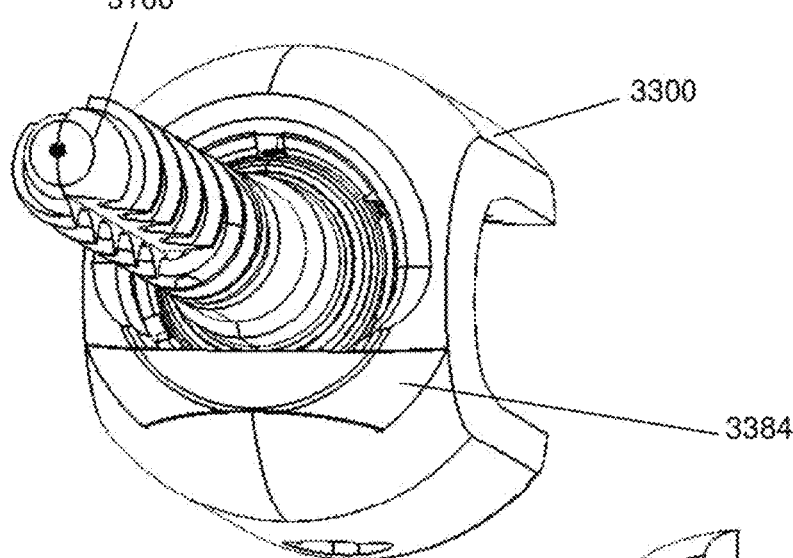

FIG. 30A is a three-dimensional perspective view of an embodiment that provides D-planar motion.

Figure 30B:
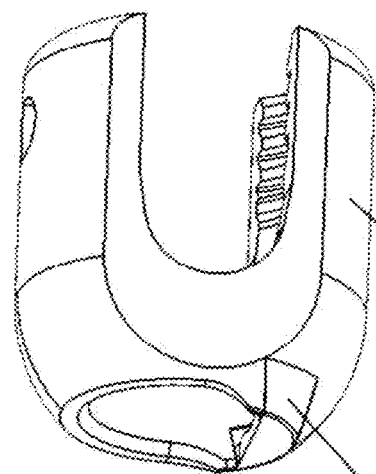

FIG. 30B is a three-dimensional perspective view of the embodiment shown in FIG. 30A, with only the movable head shown for clarity.

Figure 30C:
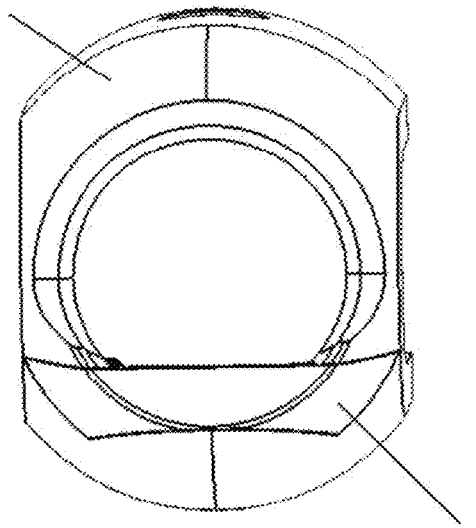

FIG. 30C is a similar view to that of FIG. 30B.

Figure 30D:
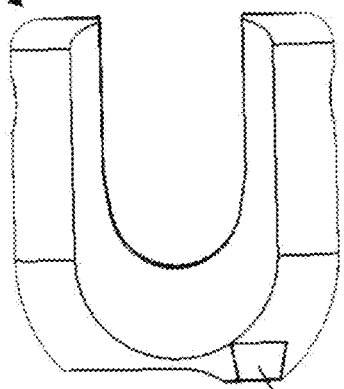

FIG. 30D is a view similar to that of FIG. 30B.

Figure 31A:
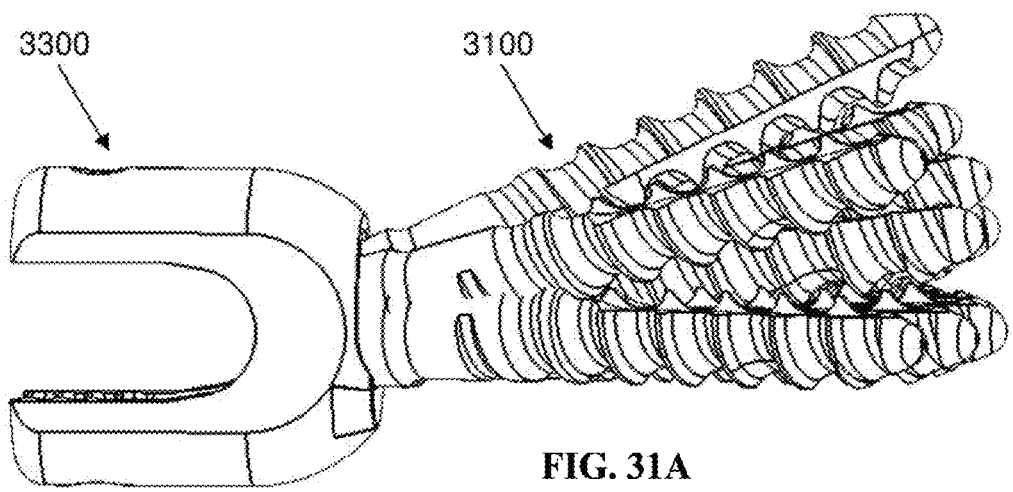

FIG. 31A is a three-dimensional perspective view of the embodiment shown in FIG. 30A, but with the screw shaft shown in multiple positions superimposed on each other to illustrate a range of motion.

Figure 31B:
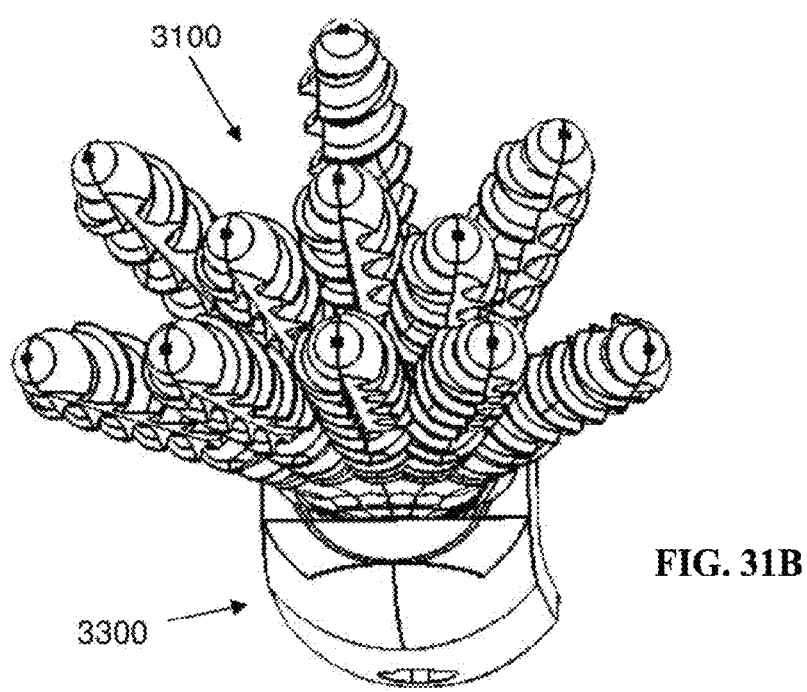

FIG. 31B is similar to FIG. 31A.

Figure 32A:
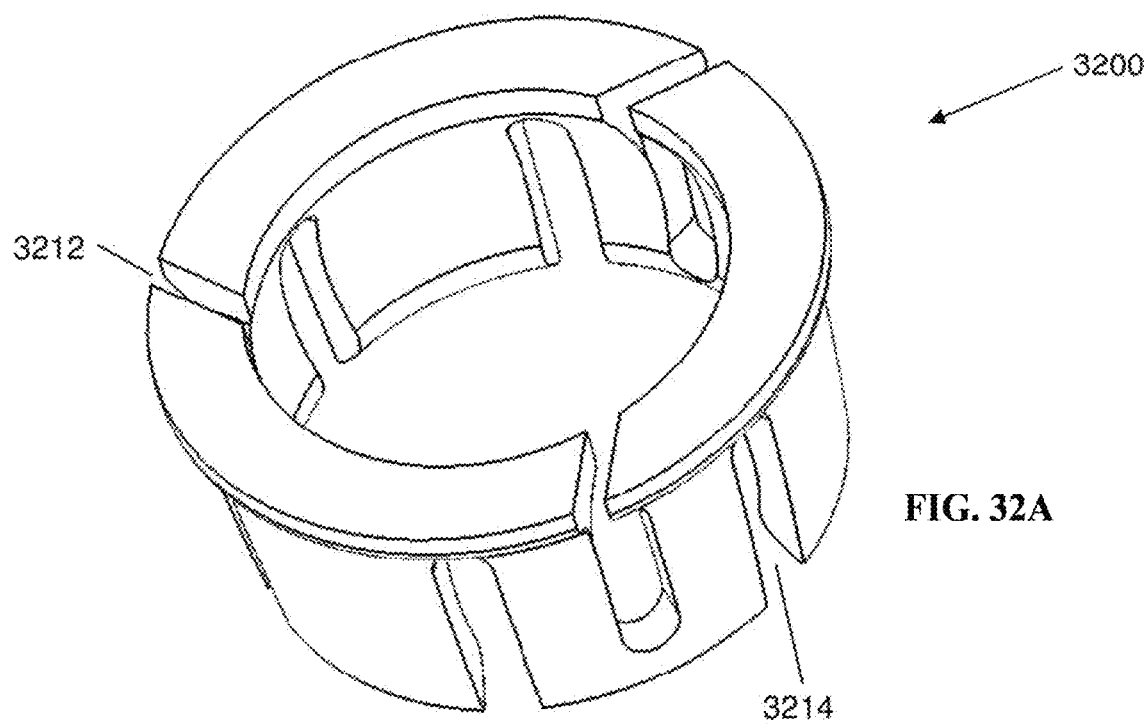

FIG. 32A is a three-dimensional perspective view of an embodiment of a collet.

Figure 32B:
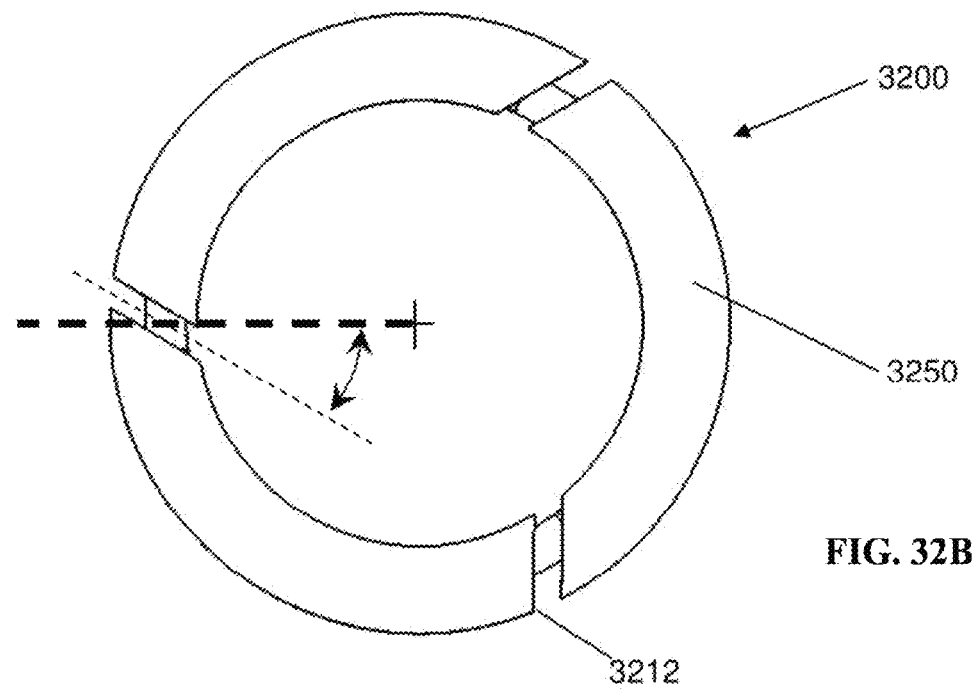

FIG. 32B is a top view of the embodiment shown in FIG. 32A.

Figure 32C:
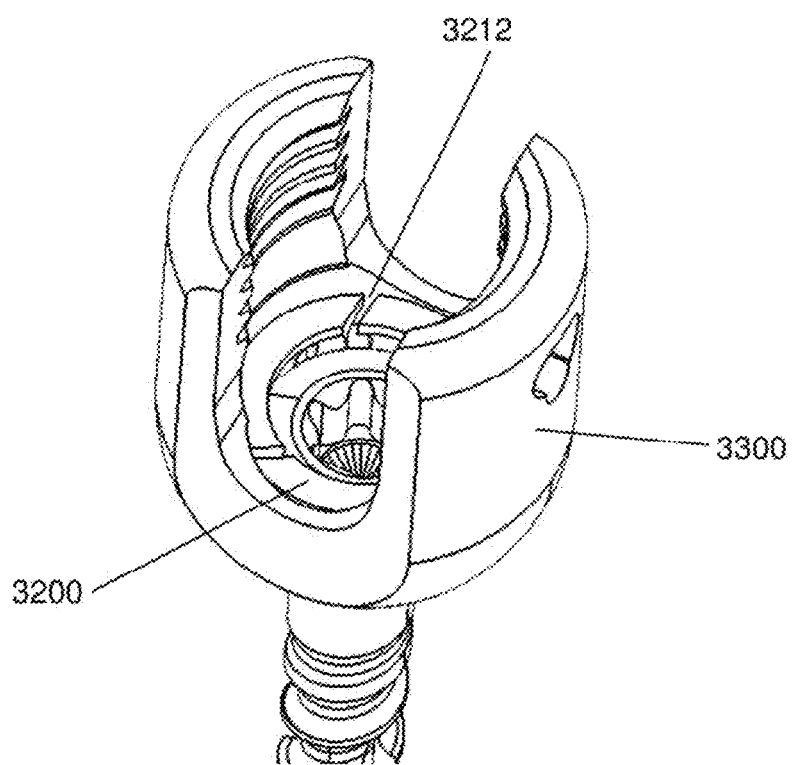

FIG. 32C is a perspective view of an embodiment of a screw apparatus with the embodiment of the collet shown in FIGS. 32A and 32B.

DETAILED DESCRIPTION

Figure 3A:
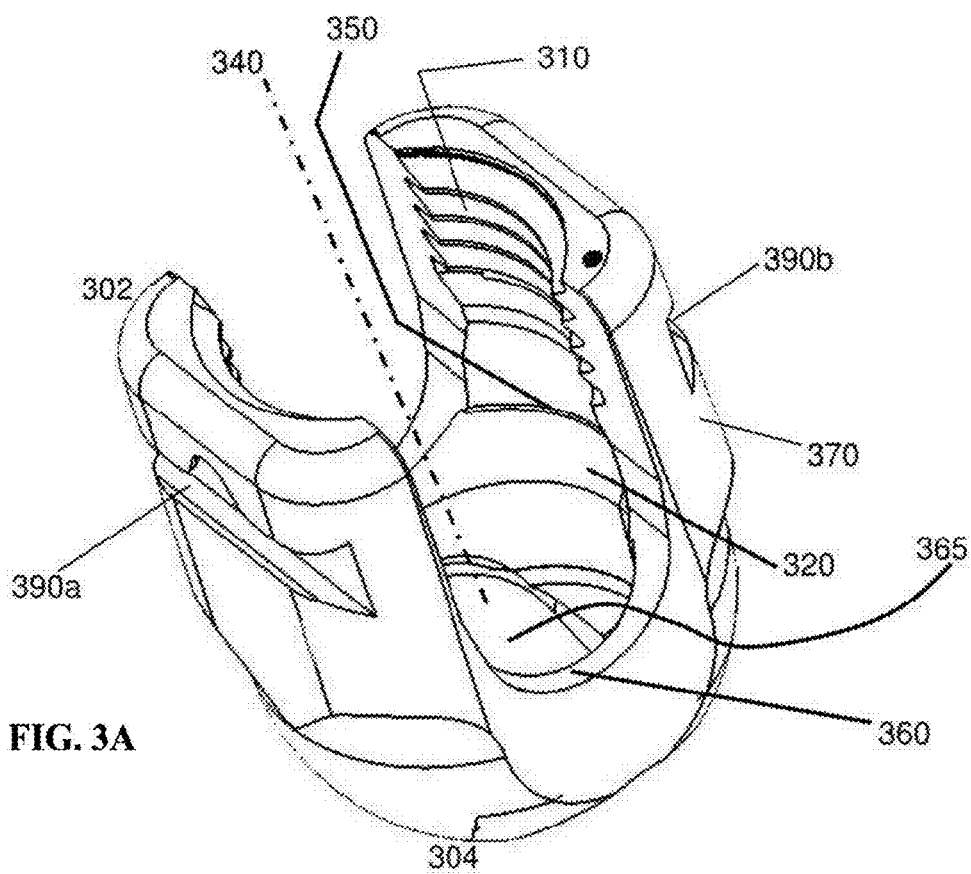
FIGS. 3A, 3B and 3C are various three-dimensional perspective views of a movable head used in an embodiment.
Figures 3B, 3C:
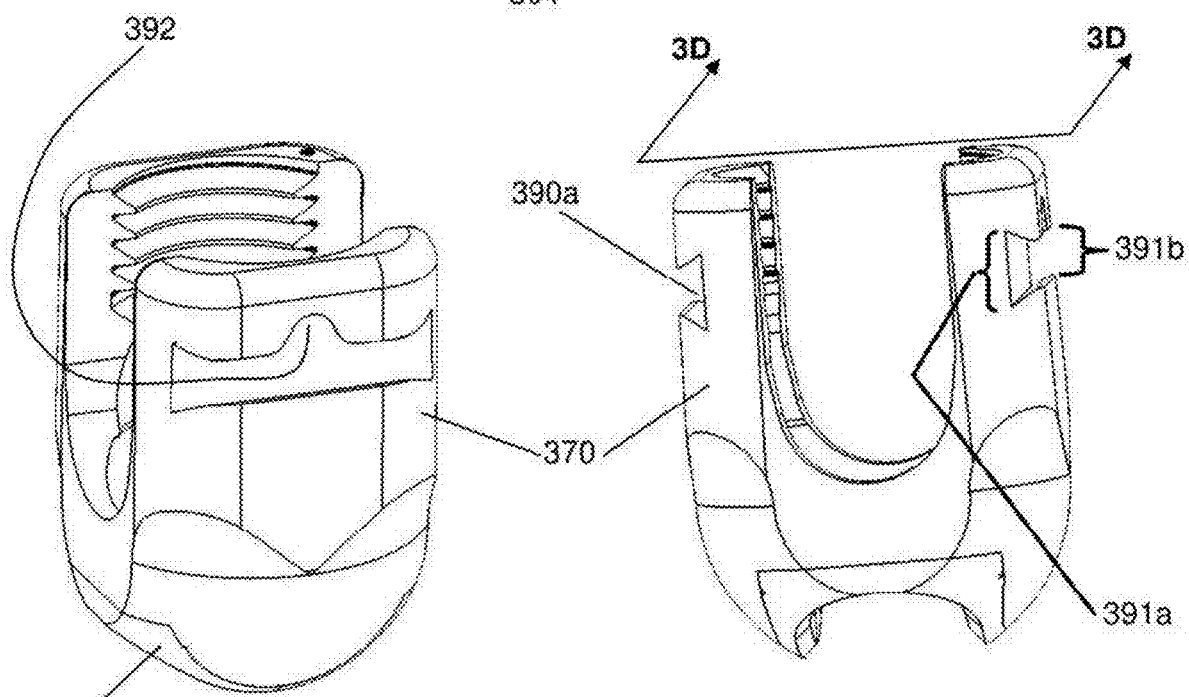

Embodiments may further be understood with reference to the various Figures. With reference to FIGS. 1, 2, and 3, an embodiment provides a screw 100 that may possess a shaft 110, and a screw head 130 that may be integral with or attached to the shaft 110. The screw head 130 may be a portion of a sphere or have a spheroidal shape. The apparatus may further be provided with a collet 200 that may fit around all or a portion of the screw head 130. The apparatus may further have a movable head 300, which may in turn fit around the collet 200.

Screw

Referring now to FIG. 1A and FIG. 1B in additional detail, screw 100 may possess threads 120 around shaft 110. Screw head 130 may also have, at its end opposite shaft 110, a tool interface recess 136 (see, e.g., FIGS. 16C-16F) that may be a hexalobe feature. Screw 100 may have a longitudinal axis 140. The longitudinal axis 140 generally extends through the center of the screw 100 along its length. In the vicinity of longitudinal axis 140, the screw shaft 110 may be either solid (as illustrated) or alternatively may be hollow, with the empty central region being available for other purposes as may be desired. Other than tool interface recess 136 and features related to threads 120, the screw 100, including the screw head 130, may be axisymmetric about longitudinal axis 140.

Collet

Referring now to FIGS. 2A and 2B, there may be provided with a collet 200 having a generally ring shape defining a central opening 208 and a longitudinal axis 240. The collet 200 may have a first or top end at a proximal end 202 of the collet 200 and a second or bottom end at a distal end 204 of the collet 200. The collet longitudinal axis 240 extends through the center of the collet 200 from a proximal end 202 to a distal end 204 of the collet 200. The collet 200 may have slots 210 that may be provided in an alternating pattern around the circumference. Such a slot pattern may provide the collet 200 with the ability to elastically deflect in any of various directions. For example, the collet 200 may, within certain limits, be deformable radially inwardly and may be deformable radially outwardly. Bending or twisting of the collet 200 in various directions may also be permitted.

It is further possible that the collet 200 may, when in an undeformed state, have a collet inner surface 220 that may be partially spherical and may resemble a portion of the external surface of the screw head 130. However, the collet inner surface 220 does not need to exactly match the external surface of the screw head 130. More generally, the collet inner surface 220 may be concave with a less tight curvature (that is, a larger radius of curvature) than the spherical portion of the screw head 130. The collet inner surface 220 and the screw head 130 may be related to each other such that when the collet 200 is constrained against outward radial deformation, the screw head 130 is prevented from sliding distally with respect to the collet 200, such as by a wedging action. For example, as illustrated in FIG. 2B, the inside surface of the collet 200 may have an inside radius (measured from centerline axis 240) of R1 near the proximal end 202, and may have another inside radius R2, and may have a third inside radius R3 near the distal end 204. R2 may be measured somewhere between the measurement locations of R1 and R3. R2 may be the largest radius of the three radii. Also, the exterior of the collet 200 may have an external taper 201 or curvature such that the collet exterior is narrower toward the distal end 204 of the collet 200 as compared to the proximal end 202 of the collet 200.

It is further possible that the collet 200 may have a collet external surface 230, which may resemble an internal surface 325 of the movable head 300. At least a portion of the collet external surface 230 may be frustoconical. In FIG. 2B, the overall included angle of the external taper of collet 200 is labeled using the designation a (alpha). However, the collet external surface 230 need not exactly match internal surface 325 of movable head 300 or any other internal surface of the movable head 300.

The collet 200 may be capable of deforming radially outwardly so as to receive the screw head 130, and may be capable of springing radially inwardly after the screw head 130 is in an appropriate place inside the collet 200.

The collet 200 and screw head 130 may be related such that when the collet 200 fits around the screw head 130 in the absence of movable head 300, with no external forces being applied, the collet 200 is snug against the screw head 130 resulting in friction between the collet 200 and screw head 130. The collet 200 and screw head 130 may be related such that when the collet 200 fits around the screw head 130 in the presence of movable head 300 in the fully-assembled configuration but without a spinal rod tightened into place, the collet 200 is snug against the screw head 130 resulting in friction between the collet 200 and the screw head 130. This friction may be such that the movable head 300 can be placed in any desired position relative to the screw 100 within the range of permitted motion and will remain in that position at least against gravitational forces acting on the various parts of the screw assembly (i.e., the individual weight of the various parts) in any orientation. The friction may be greater than what is needed simply to maintain a position of the screw 100, relative to the movable head 300, against gravitational forces.

The collet 200 may further have an external lip 250 at or near its proximal end. Such an external lip 250 may extend farther outwardly in a radial direction than the rest of the collet 200. The external lip 250 may be interrupted by the slots 210 just as nearby parts of the collet 200, other than the external lip 250, are interrupted by the slots 210.

Movable Head

Referring now to FIGS. 3A-3D, movable head 300 may have a proximal end 302 and a distal end 304 and a generally longitudinal axis 340 from the proximal end 302 to the distal end 304 through the center of the movable head 300. The movable head 300 may also have a first or top portion or end and a second or bottom portion or end, whereby the top portion is located at a proximal end 302 of the movable head 300 and the bottom portion is located at a distal end 304 of the movable head 300. The movable head 300 may have an internal thread 310 at its proximal end 302. The movable head 300 may also have, at its proximal end 302, a U-shaped passageway or U-trough 360 through the movable head 300. The U-trough 360 may have an axis generally perpendicular to the longitudinal axis 340 of the movable head. The U-trough 360 axis may also be generally transverse through the movable head 300. The movable head 300 may have a hole 365 therethrough at its distal end or bottom portion.

Figure 3D:
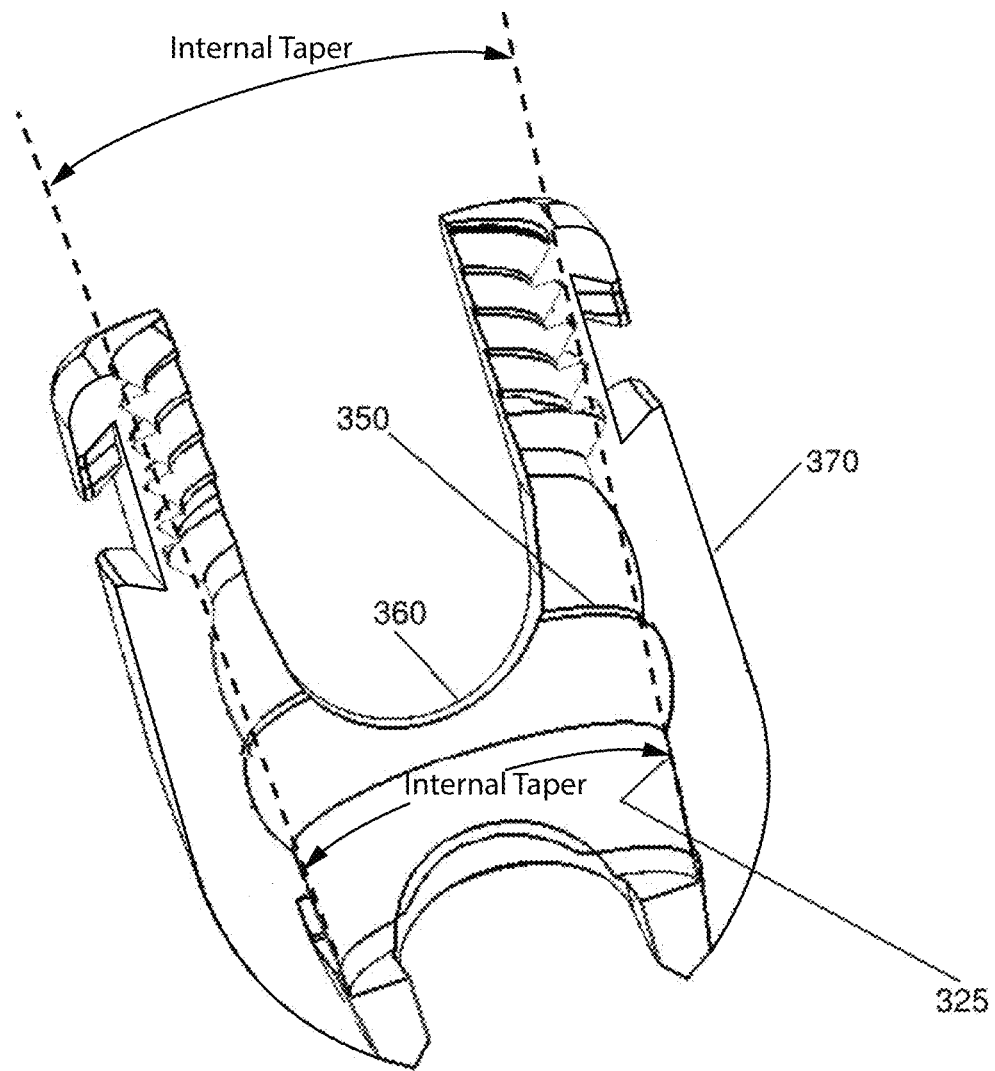
FIG. 3D is a cross-sectional view of the embodiment shown in FIGS. 3A, 3B, and 3C.

The movable head 300 distal end 304 may have an internal surface 320 located between the internal thread 310 and the hole 365 at the distal end 304. The internal surface 320 may be generally concave and may be at least partially spherical or generally spheroidal in shape. As illustrated in FIG. 3D, the movable head 300 may have an internal lip 350 between the internal surface 320 and the internal thread 340. The movable head 300 may also have an internal tapered region 325, which may be frusto-conical and may be at least somewhat complementary to the external surface 230 of the collet 200.

There may be provided, on an external surface of the movable head 300, any of a variety of interface features 390*a*, 390*b* for interfacing with a tool or instrument. Such interface features 390*a*, 390*b* may be provided on each of two opposed sides of the movable head 300. The interface features 390*a*, 390*b* may be identical to each other or symmetrical to each other about a common plane or axis, or, alternatively, there may be design differences between the interface features 390*a* and 390*b*. It is possible that either or both of the interface features 390*a*, 390*b* may have an undercut so as to provide a slip-resistant interface with the instrument or tool. As is illustrated most particularly in FIG. 3B, such an undercut may have a cross-sectional shape that is trapezoidal, with base 391*a*, the longer of the two parallel sides of the trapezoid and being closer to the longitudinal axis 340 of the movable head 300 than is opening 391*b*, the shorter of the two parallel sides. As illustrated most particularly in FIG. 3C, it is possible that either or both of the interface features 390*a*, 390*b* may have an external interface centering feature 392 that is located at a plane of symmetry of the movable head 300. The external interface centering feature may be a depression or may be a recess in a direction different from other portions of the interface features 390*a*, 390*b*.

Movable head 300 may also possess a proximal portion or component 370 and a distal portion or component 380, as described in more detail elsewhere herein.

Set Screw and Saddle

Referring now to FIG. 4, the apparatus may further be provided with a set screw 500 that may have an external thread 540 that engages with the internal thread 310 of the movable head 300. The apparatus may further be provided with a saddle 580 to form an interface between the set screw 500 and a rod 400 (described elsewhere herein). The saddle 580 may be captured by or attached to set screw 500 in such a way as to form a single assembly together with the set screw 500. However, even when captured or assembled, the saddle 580 may be able to rotate with respect to the set screw 500. Such capturing or assembly connection may be either loose or frictional as desired. Furthermore, it is possible that when the assembly of the saddle 580 and set screw 500 is provided to the user, the relative rotational position of the saddle 580 and set screw 500 may be pre-set so as to be appropriate for starting engagement of the thread of the set screw 500 with the thread 310 of the movable head 300. This thread-starting relationship is especially achievable if there is a frictional relationship between the saddle 580 and set screw 500. Thus, sliding the saddle 580 into the U-trough 360 may then serve to align the threads to their proper starting position. The rod-facing surface 590 of the saddle 580 may be at least approximately contoured to complement the corresponding surface of the rod 400 so as to provide appropriate transfer of clamping load and other loads to or from the rod 400. The rod-facing surface 590 of the saddle 580 may be either smooth or textured as desired. The external shape of the saddle 580 may be such that the saddle 580 can only be slid into the movable head 300 at certain angular positions, which may correspond to desired thread-starting positions.

It is further possible that there could be provided timing features marked on any of the nearby parts for indicating the optimal place to begin engagement of the set screw thread 540 and the internal thread 340 in the movable head 300.

Assembled (but Un-Tightened) Apparatus

These various components are shown in FIGS. 5A and 5B in a configuration in which the components have been assembled, but the apparatus is not yet tightened so as to hold a spinal rod. This may be referred to as a nominal assembled configuration. It is noted that, as illustrated in FIGS. 5A and 5B, the collet 200 is not as far advanced toward the distal end of the apparatus as it would eventually be when a rod 400 is in place and tightened. Also as illustrated in FIGS. 5A and 5B, the collet 200 is positioned such that the external lip 250 of the collet 200 is just slightly distal of the internal lip 350 of the movable head 300 (also shown in FIG. 16D-16F).

Rotation and Angulation

Referring now to FIGS. 6A-6C, a configuration of the apparatus is provided showing the position of the screw with respect to the movable head 300, with a screw assembly of an embodiment tightened to grasp a spinal rod 400.

Referring now to FIG. 6A, the illustrated apparatus shows the screw 100 is able to rotate with respect to the movable head 300 around the longitudinal axis 140 of the screw 100. The apparatus may be such that the screw 100 is able to rotate about the longitudinal axis 140 without constraint, i.e., even more than one full rotation if desired. It is possible, although it is not wished to be limited to this example, that when such motion occurs, the screw head 130 rotates with respect to the collet 200 while the collet 200 remains stationary with respect to the movable head 300. However, it is also possible that the opposite may happen, i.e., the screw head 130 and the collet 200 could rotate as a unit with respect to the movable head 300. Furthermore, it is even possible that some rotation at each interface could occur.

It can further be observed that for the apparatus as illustrated, the screw head 130 is able to angulate with respect to the movable head 300 around at least one additional axis that is not coincident with the screw longitudinal axis 140. However, there may be constraints against such angulation in certain directions, as described below.

Limits on Angulation

With continuing reference to FIGS. 6A-6C, the apparatus may be configured such that it permits, within certain limits, angulation of the screw 100 with respect to movable head 300. The limits of angulation may be such as to define a space of permitted angles that make up a shape which is not a cone. The limits of angulation may be defined quite specifically by the shape of the edges of the distal portion 380 of the movable head 300 (such as sub-motion-limiters 382, 384). Angulation limits may be defined with respect to each of two different planes or rotational axes, which may be mutually perpendicular to each other. These amounts of angulation may be, and preferably are, different from each other. As illustrated in FIG. 6B and FIG. 6C, a substantial amount of angulation of the screw 100 relative to the movable head 300 is permitted in the degree of freedom illustrated in FIG. 6B, while little or no angulation of the screw 100 relative to the movable head 300 is permitted in the degree of freedom illustrated in FIG. 6C.

Referring now to FIG. 6B, it is further possible that the axis of the rod 400 may lie in or may be parallel to the defined plane of angulation in which substantial angulation is permitted. However, it is also possible that there could be other relations between the plane of substantial permitted angulation and the axis of the spinal rod 400.

Figure 8A:
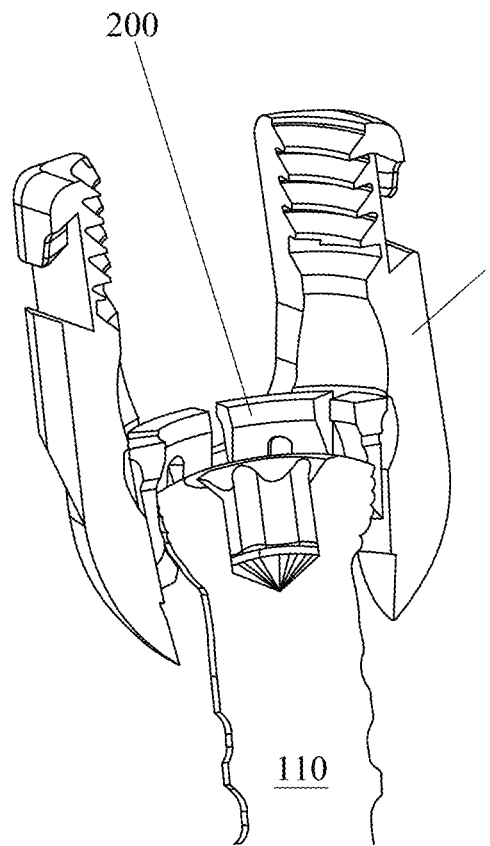
FIG. 8A is a perspective view of a cross-section of the movable head and the screw and the collet, in the absence of the distal portion of the movable head.
Figure 8B:
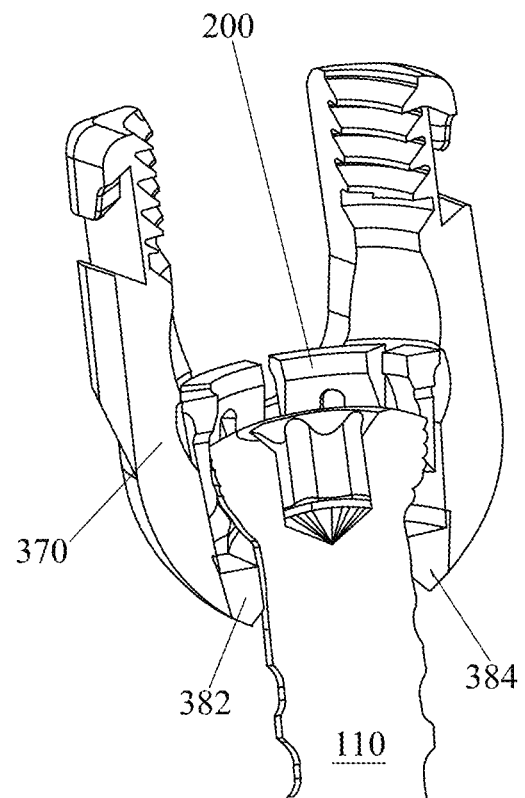
FIG. 8B is a perspective view of a cross-section of the movable head and the screw and the collet, in the presence of the distal portion of the movable head.
Figure 12:
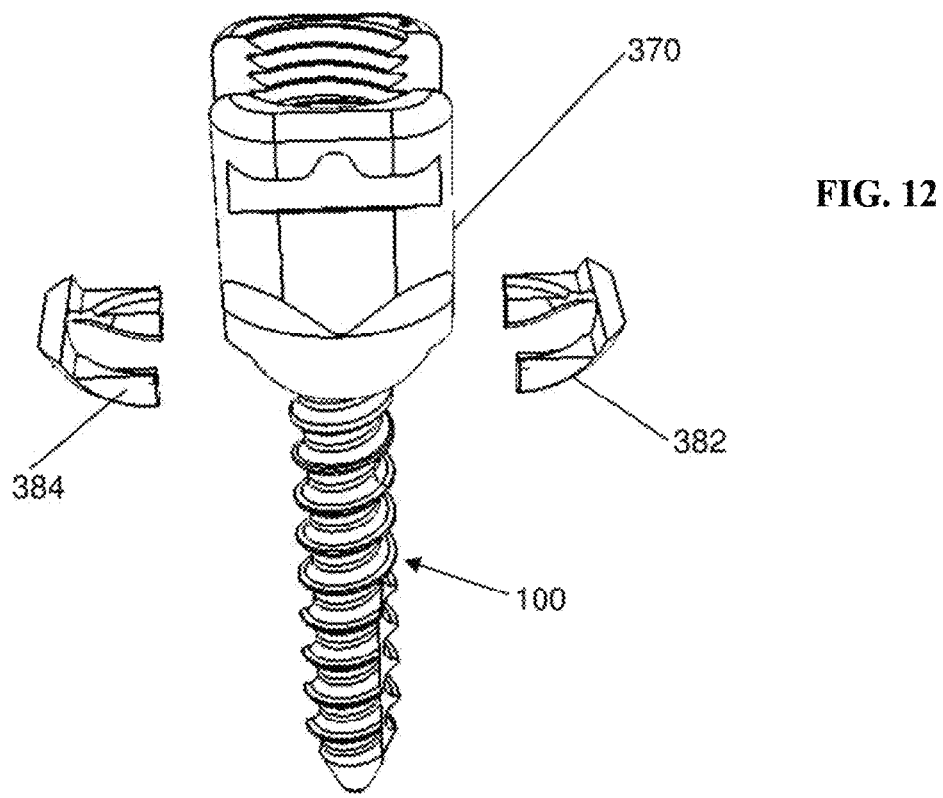
FIG. 12 is a perspective view similar to FIG. 11 but showing two sub-motion-limiters about to slide into place, from yet another viewing angle.

It is further possible that there may be defined a baseline position of the movable head 300 relative to the screw longitudinal axis 140 such that the longitudinal axis 340 of the movable head 300 might, when in this baseline position, coincide with the screw longitudinal axis 140, as is illustrated in FIGS. 8A, 8B and 12. This baseline position may also be such that the screw is in all respects in the middle of the range of permitted angulation positions. However, it is not essential that the longitudinal axis of the movable head 300 coincide with the middle of the range of angulation. If desired, it may also be possible to design the screw assemblies such that the baseline position of the movable head axis 340 is biased. In other words, the baseline position does not have to be coincident with the screw longitudinal axis 140 at the middle of the range of angulation.

Details about Angulation-Limiting Components

Figure 7:
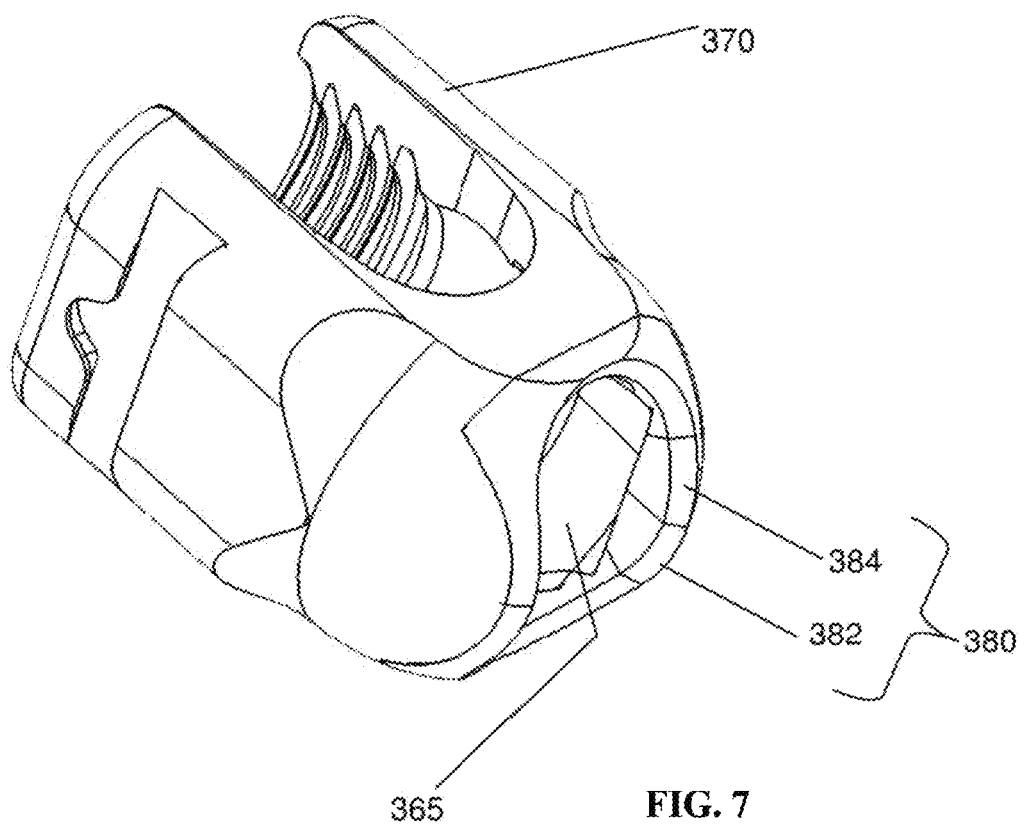
FIG. 7 is a perspective view of a movable head of a disclosed embodiment.

Referring now to FIG. 7, the movable head 300 may be provided with a proximal portion or component 370 and a distal portion or component 380 that may be assembled to each other for purposes of achieving limits of angulation of the screw shaft 130. It is possible that distal portion 380 could be made as a single component if appropriate provision is made for joining the distal portion 380 to the proximal portion 370. For example, the distal portion 380, if made as a single component, might be welded to the proximal portion 370 but without the benefit of a mechanical interlock, i.e., with the weld being the major path for transferring mechanical load from distal portion 380 to proximal portion 370.

The distal portion 380 will be first discussed as a single component. The opening through the distal portion 380 may help to determine the permitted angulation of the screw shaft 130 with respect to polyaxial the screw head 300. The distal portion 380 may define a distal opening 365 through the movable head 300. The distal opening 365 may have a non-round shape. For example, the distal opening may have an elongate circular or racetrack shape. The distal opening 365 may be such that when the various components are assembled, the distal opening 365 limits angulation of the screw 100 relative to movable head 300. The distal opening may be such as to permit angulation within defined limits within a first plane and essentially forbid angulation in a second plane that is perpendicular to the first plane. Alternatively, the distal opening may be such as to permit a defined amount angulation in a first plane and permit only a relatively smaller defined amount of angulation in a second plane that is perpendicular to the first plane.

FIG. 8A shows proximal portion 370 and the screw head 130, but distal portion 380 is not shown. FIG. 8B shows proximal portion 370, distal portion 380 and the screw head 130.

Figure 8C:
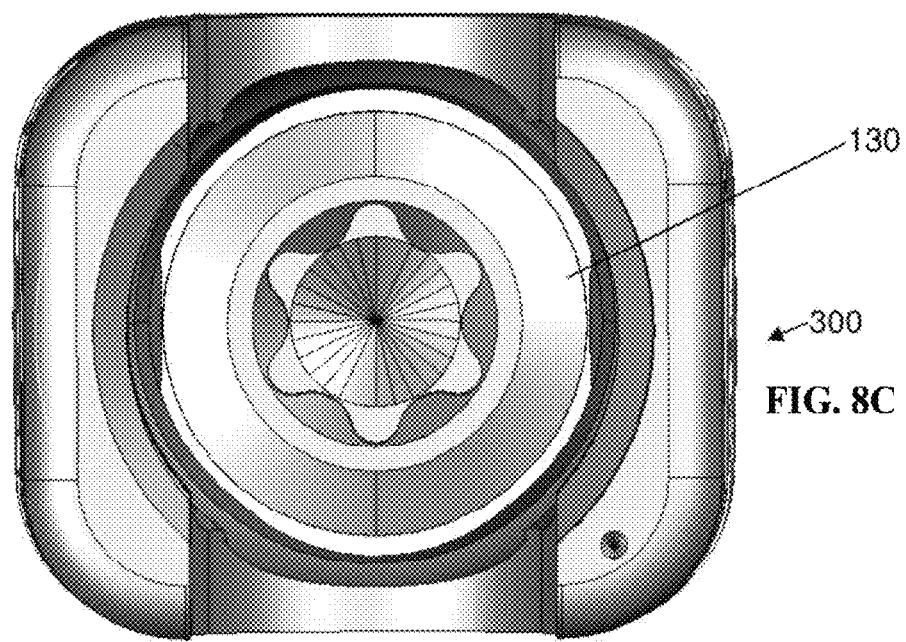
FIGS. 8C, 8D, 8E and 8F are various views, nearly along the axis, of assemblies similar to those of FIGS. 8A and 8B.
Figure 8D:
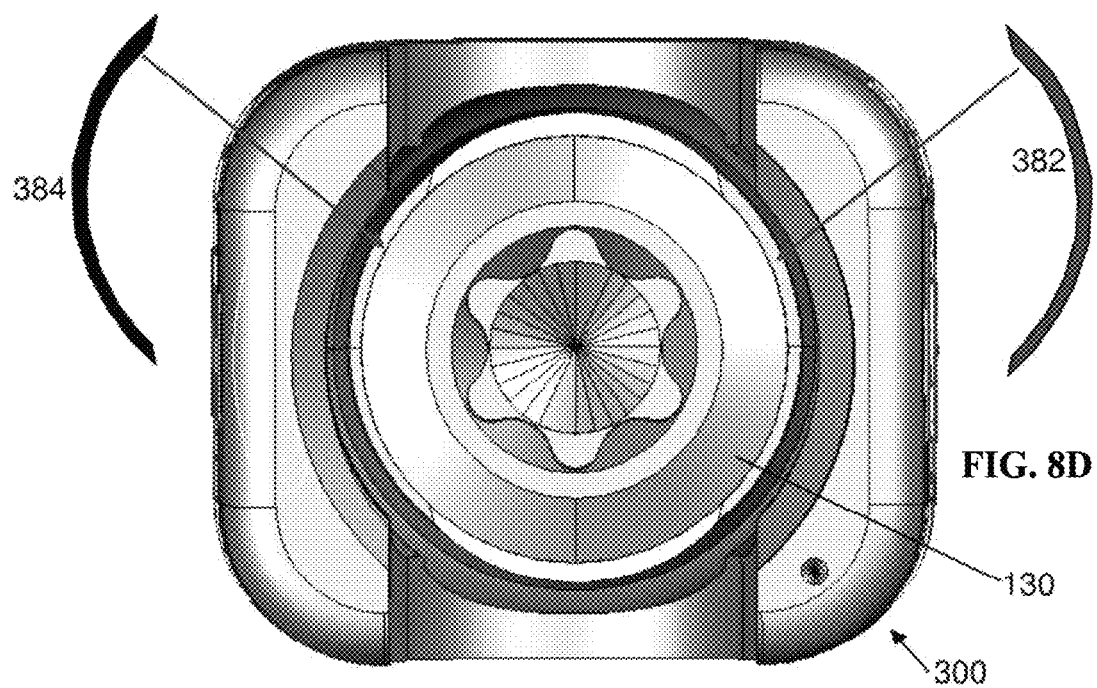
Figure 8E:
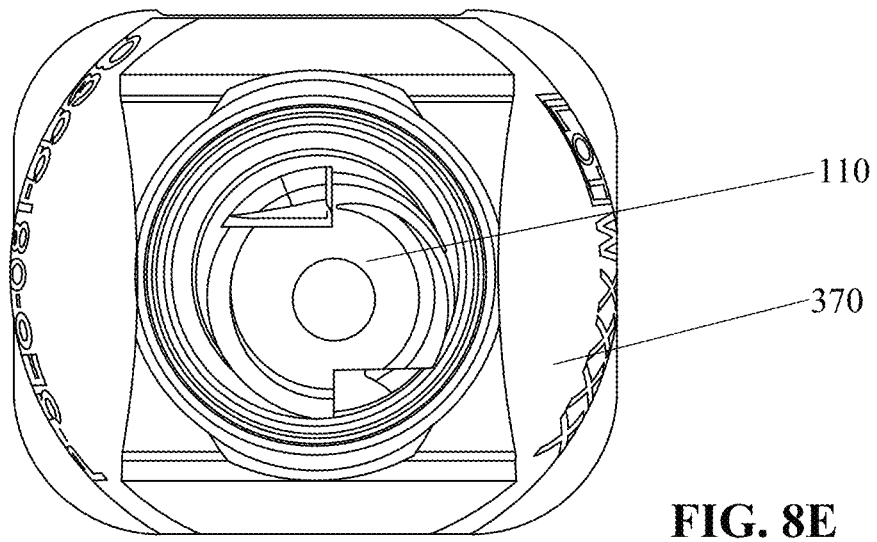
Figure 8F:
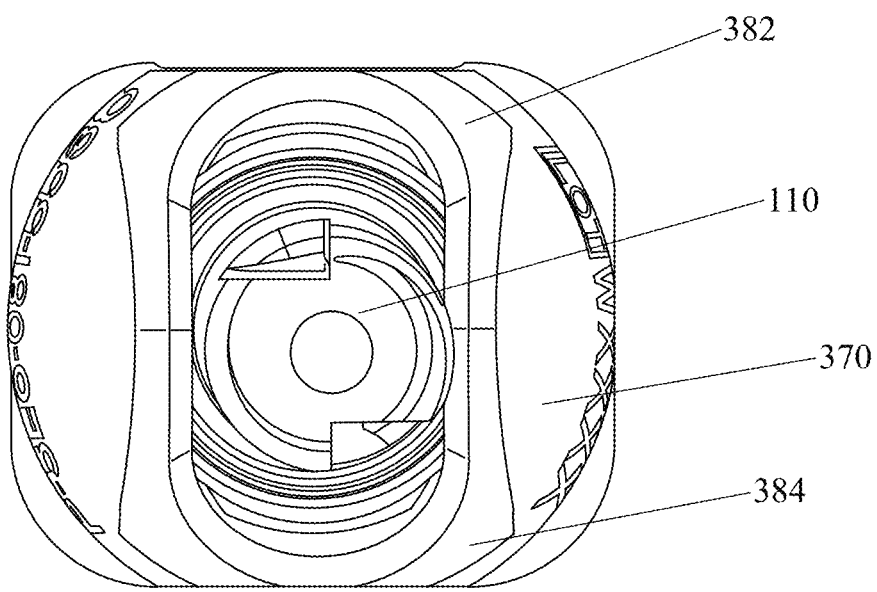

FIGS. 8C-8F, show, for purposes of illustration, the arrangement of movable head 300 and the screw 100, with the collet 200 omitted for clarity of illustration. These illustrations are views approximately along the axis 140 of the screw 100. FIGS. 8C and 8D are views looking from the proximal end to the distal end, and FIGS. 8E and 8F are views from the distal end to the proximal end. In FIG. 8C, the sub-motion-limiters 382, 384 are omitted and it can be observed that there is empty space completely around the screw head 130 between the movable head 300 and the screw head 130, which illustrates that the screw head 130 has an unrestricted path to come up into the movable head 300 for assembly purposes. The same situation is visible in FIG. 8E from a different vantage point. In FIG. 8D, the two sub-motion-limiters 382, 384 are present, and a small visible portion of sub-motion-limiters 382, 384 is highlighted. In FIG. 8F, from a different vantage point, sub-motion-limiters 382, 384 are visible in their entirety, and therefore empty space is visible at only some places around the circumference of the screw head 130, but is not visible around the entire circumference of the screw head 130. In FIGS. 8D and 8F, empty space is visible between the movable head 300 and the screw head 130 in two places but not all the way around the circumference. The empty space which is visible is related to the range of permitted motion. The places where empty space is not visible are related to the trapping of the screw head 130 within movable head 300. In this situation, the sub-motion-limiters 382, 384 may contribute to trapping the screw head 130 within the movable head 300, although the collet 200 (not present in FIG. 8C-8F) may also be involved in direct contact with the screw head 130.

Figure 9A:
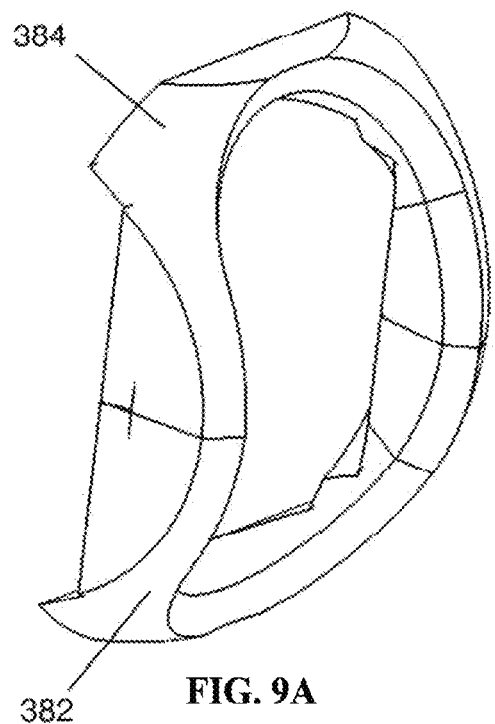
FIG. 9A is a perspective view of only the distal portion of the movable head, having two sub-motion-limiters.
Figure 9B:
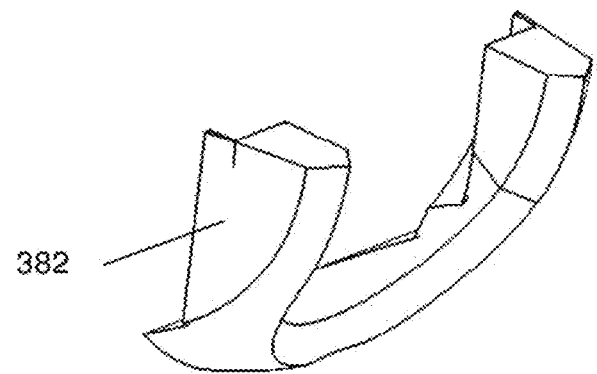
FIG. 9B is a perspective view of only one sub-motion-limiter.

Referring now to FIGS. 9A and 9B, it is possible that the distal portion 380 may be provided with two sub-motion-limiters 382, 384 which together make up distal portion 380. The sub-motion-limiters 382, 384 may be identical to each other, or symmetric to each other about a common plane that generally lies between the sub-motion-limiters 382, 384 so that each one makes one-half of distal portion 380. Such subdividing of distal portion 380 into sub-motion-limiters 382, 384 may be done such as to facilitate assembly as discussed elsewhere herein.

Figure 10:
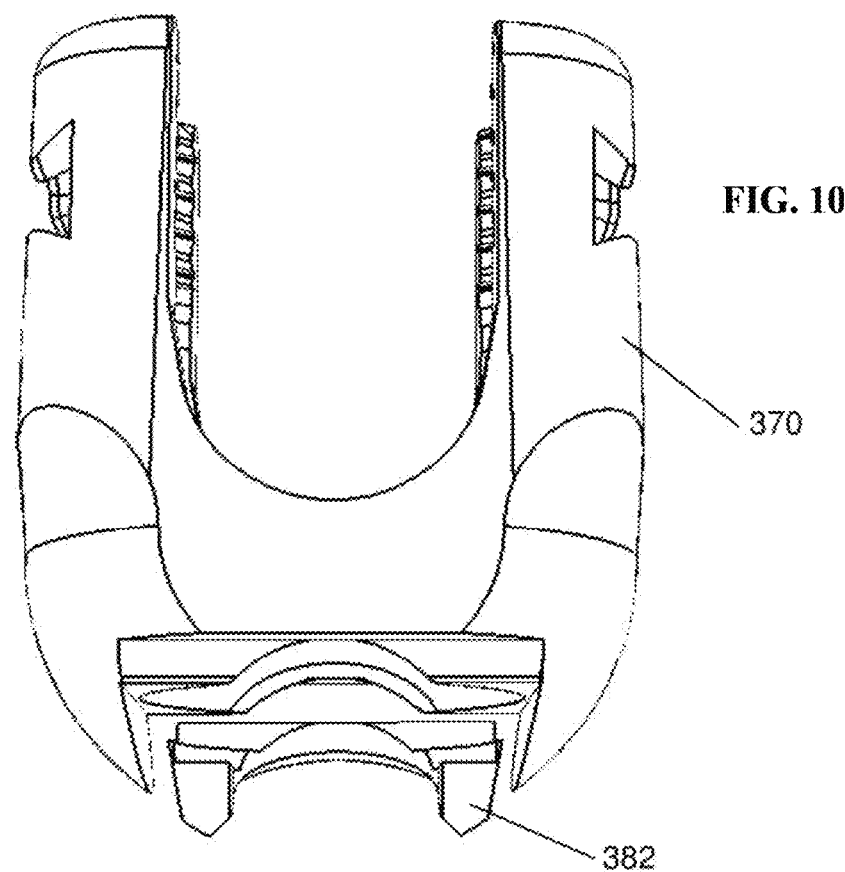
FIG. 10 is a perspective view of a sub-motion-limiter and a proximal portion of the polyaxial screw head, showing a sub-motion-limiter about to slide into place in the movable head.

Referring now to FIG. 10, the interaction between the sub-motion-limiter 382 and the polyaxial the screw head proximal portion 370 is shown. The sub-motion-limiter 382 is adapted to slide, along a direction of sliding insertion, into a receiving feature in the proximal portion 370 of the movable head 300. The direction of sliding insertion is generally parallel to an axis through the U-trough 360 (an axis generally following a longitudinal axis of rod 400 as shown at least in FIG. 6A), and also generally perpendicular to the longitudinal axis 340 of the movable head 300. Though, this example is not intended to be limiting, for instance, the direction of sliding insertion may be skew to an axis of the U-trough, or at an angle to the longitudinal axis 340 of the movable head that is less than perpendicular. FIG. 10 is a perspective view, in which sub-motion-limiter 382 is positioned some distance behind the movable head 300. As a result, the sub-motion-limiter 382 appears narrower in width than a corresponding dovetail feature in the movable head 300. However, this only appears as such because of the perspective nature of the illustration, and the orientation of the view. The design of the sub-motion-limiter 382 and the design of the proximal portion 370 may be such that the sub-motion-limiter 382 is mechanically captured within the proximal portion 370. Such geometry could thereby restrain the sub-motion-limiter 382 against possible motion or forces along the longitudinal axis 340 of the movable head 300, such as forces that would act to separate the sub-motion-limiter 382 from the proximal portion 370. In some embodiments, the interaction between sub-motion-limiter 382 and proximal portion 370 may have a dovetail joint. For example, the sub-motion-limiter 382 (or 384) may have a taper such that the sub-motion-limiter 382 is wider at its proximal end and narrower at its distal end, and the proximal portion 370 of the movable head 300 may have a complementary taper, such as, for example, a dovetail feature 372. As a result of these tapers, the sub-motion-limiter 382 (or 384) and the proximal portion 370 may form a dovetail joint connection capable of resisting separation that could be caused by forces applied to the distal portion 380 along the longitudinal axis 340 of the movable head 300. Of course, as an alternative to the dovetail joint 372, a shelf relationship, such as a shelf or step joint, could also be used for the same purpose. Clips or other retention features could be provided so that when the sub-motion-limiter 382 (or 384) is in place in the proximal portion 370 it is discouraged from coming out of place. It would also be possible that there be a press fit between any of the relevant components to retain the components in place. Similarly, it would be possible that some deformation is required to occur in order for the components to be assembled. Welding, such as laser-welding, could also be used in attachment of sub-motion-limiter 382 (or 384) to the proximal portion 370 either in addition to the described mechanical interlock, or in place thereof.

Figure 11:
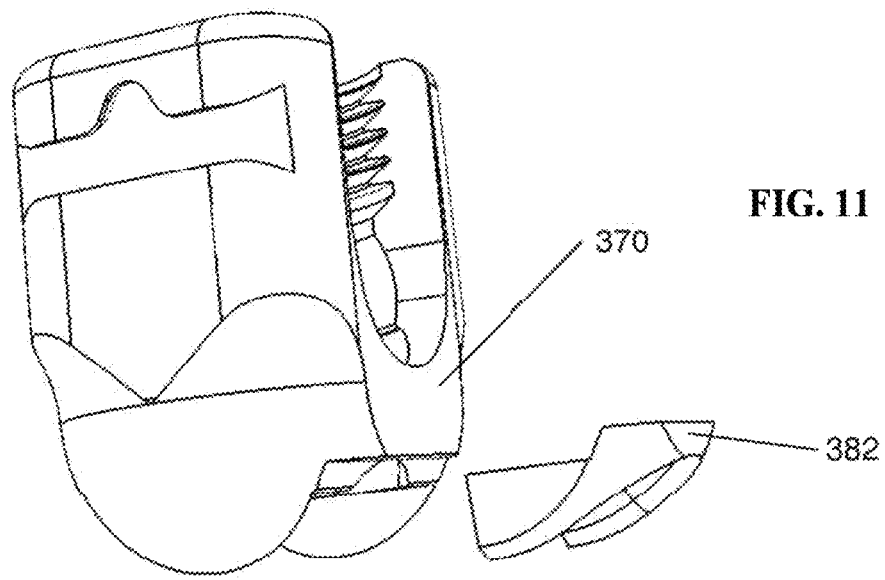
FIG. 11 is a perspective view similar to FIG. 10, but from a different viewing angle.

FIG. 11 also illustrates the ability of the sub-motion-limiter 382 to slide into the proximal portion 370, but viewed from a different perspective. FIG. 12 also illustrates this, but shows both sub-motion-limiters 382 and 384 as if they were about to slide into place (also showing the screw 100 already in position).

Referring now to FIGS. 13A and 13B, there is further illustrated the possible taper or dovetail relationship between sub-motion-limiter 382 or 384, and proximal portion 370, particularly dovetail 372. FIG. 13A is a view of sub-motion-limiter 382, showing the taper angle. FIG. 13B is a view of sub-motion-limiter 382 and also proximal portion 370 with taper angles identified on both pieces. It can be seen that the taper angles on the respective pieces 382 and 370 are equal to each other or, more generally, are almost equal to each other.

Figure 14A:
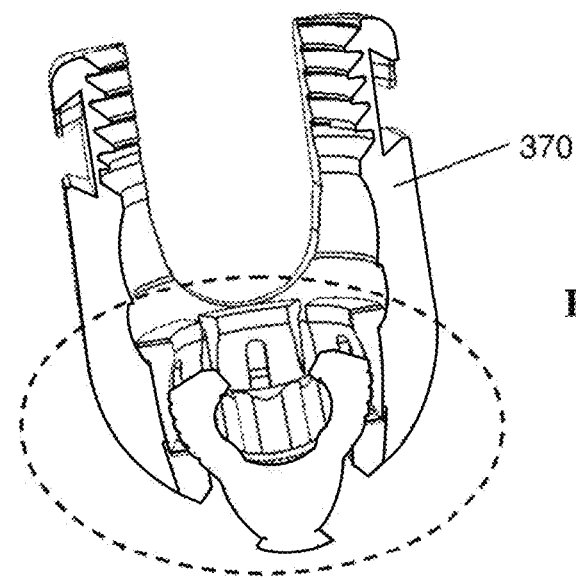
FIG. 14A is a perspective view of a cross-section of a uniplanar screw assembly.
Figure 14B:
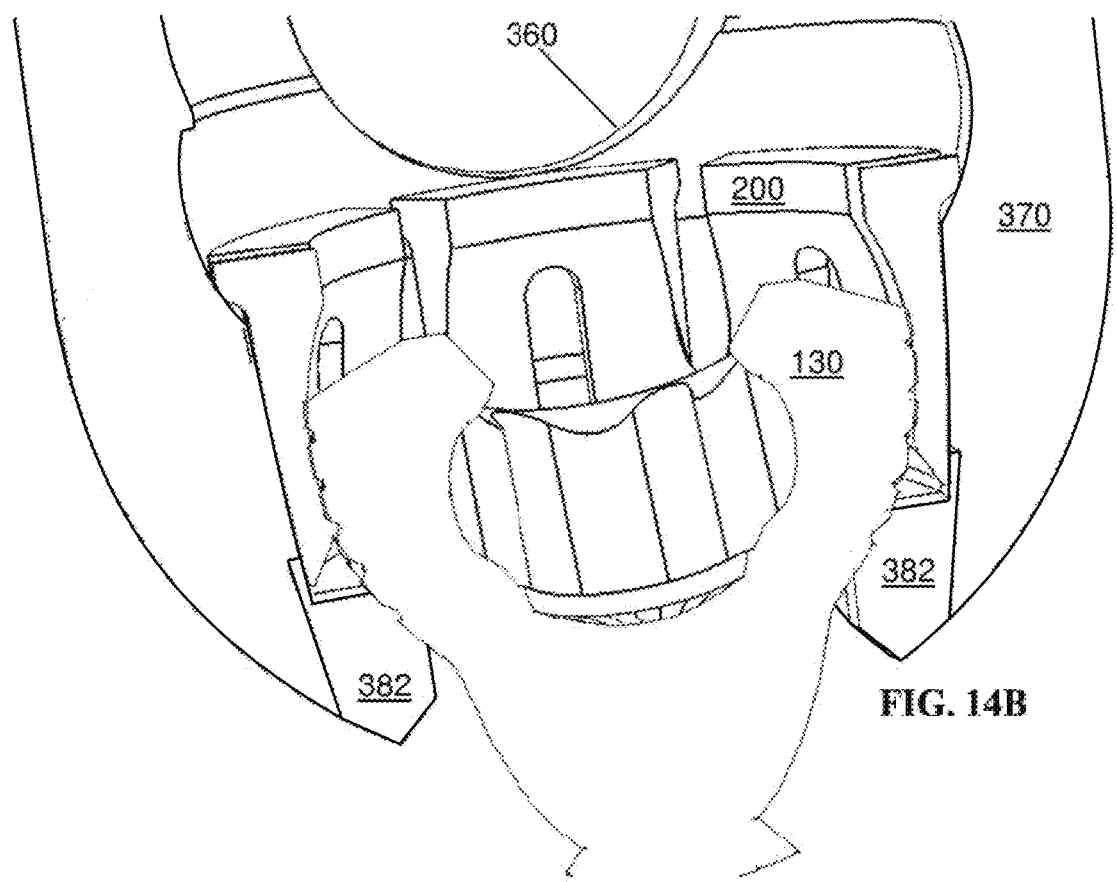
FIG. 14B is a close-up view of a portion of FIG. 14A.
Figure 15:
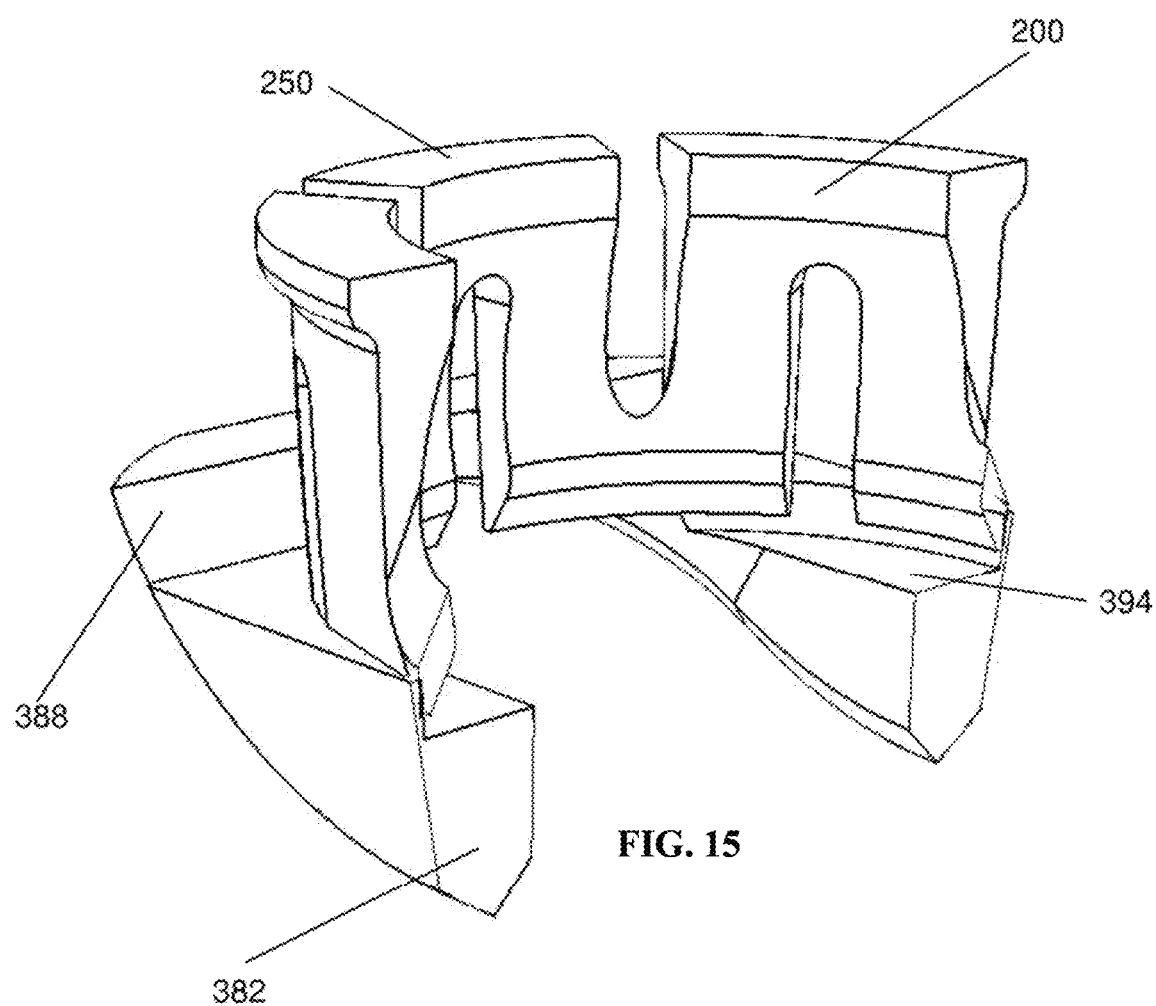
FIG. 15 is a three-dimensional perspective view of a sub-motion-limiter and also a collet in a typical position relative to the sub-motion-limiter.

Referring now to FIGS. 14A, 14B and 15, the distal portion 380 or sub-motion-limiters 382, 384 may have a recess 394 suitable to provide space for a portion of the collet 200. If there are sub-motion-limiters 382, 384, each of the sub-motion-limiters may have such a recess. The recess 394 may be such that when all the components are assembled, there is a gap between the most-distal end surface of the collet 200 and the facing surface of the recess 394 in the sub-motion-limiter. Thus, there may be provided room for the collet 200 to find its tightened position as determined by the wedging of the collet 200 external surface against the internal surface of distal portion 380 (sub-motion-limiters 382, 384) of movable head 300. It is also illustrated in FIG. 15 that the sub-motion-limiters 382, 384 may have a stop feature 388 that cooperates with the proximal portion 370 to determine how far towards the centerline 340 the sub-motion-limiters 382, 384 are allowed to slide. Thus, the stop feature 388 may determine the final position of sub-motion-limiters 382, 384 relative to proximal portion 370, especially in a direction along the direction of motion by which sub-motion-limiters slide into their final position in proximal portion 370.

The various parts may fit together such that in a fully assembled and tightened condition, a force from the set screw 500 is exerted (possibly through the saddle 580) onto a spinal rod 400, which in turn exerts force onto the proximal end surface 250 of the collet 200 which urges the collet 200 farther into the tapering interior of proximal portion 370. This may create a wedging action involving the interior of the proximal portion 370, the collet 200, and the screw head 130. Such a wedging action may lock all of the relevant components into a fixed position.

The apparatus may further have a joint, such as, for example, a weld for joining the sub-motion-limiter 382, 384 and the proximal portion 370, but such joint need not carry all of the force transmitted through the joint because of the presence of a dovetail relationship or similar supporting relationship between the sub-motion-limiter 382, 384 and proximal portion 370.

Dimensional Interrelationships and Sequence of Assembly

The apparatus may have features that provide for mechanically trapping the collet 200 within the movable head 300 when the collet 200 is deeper than a certain point within the movable head 300. For example, the internal lip 350 may be such as to interact with the external lip 250 of the collet 200 so as to trap the collet 200 inside the movable head 300. In order for the external lip 250 of the collet 200 to pass by the internal lip 350, as the collet 200 moves toward the distal end of the movable head 300, it may be possible for the external lip 250 and the collet 200, in general, to deform radially inwardly towards the longitudinal axis 240 of the collet 200. It is also possible that after the external lip 250 passes the internal lip 350, moving in a direction toward the distal end of movable head 300, the external lip 250 may spring radially outwardly. This outwardly springing action may trap the collet 200 inside the movable head 300, or at least may help to define a preferred or maintained position of the collet 200 relative to the movable head 300 when the collet 200 is in that region of the movable head 300.

The apparatus may be such that the screw (particularly the screw head 130) may be loaded into the movable head proximal portion 370 from the distal end when the distal portion 380 or the sub-motion-limiters 382, 384 are absent from the apparatus. More specifically, the diameter of the sphere of the screw head 130 may be smaller than an opening in the distal end of the movable head 300, when the distal portion 380 or the sub-motion-limiters 382, 384 are absent from the apparatus. The dimensions of the various components may further be such that when the distal portion 380 or the sub-motion-limiters 382, 384 are together with the rest of polyaxial the screw head 300, the sphere of the screw head 130 cannot fit through the distal end opening of the apparatus. It is further possible that the sphere of the screw head 130 may be too large to fit through the opening in the proximal end of the proximal portion 370.

Dimensional interrelationships among the various components may be such that, when the distal portion 380 is absent, the screw head 130 may be able to pass upwardly through the opening 365 in the distal end of the proximal portion 370 of the movable head 300. Furthermore, when the distal portion 380 is in place connected to the proximal portion 370 of the movable head 300, the screw head 130 may be unable to pass through the opening in the distal portion 380; but the screw shaft 110 is able to pass through the hole in the distal portion 380. It is possible that the screw head 130 is unable to pass through the most proximal end of the collet 200 (the end having lip 250) when the collet 200 is in place inside the movable head 300.

The collet 200 may be able to enter the movable head 300 through the open proximal end of the movable head 300.

Figure 16A:
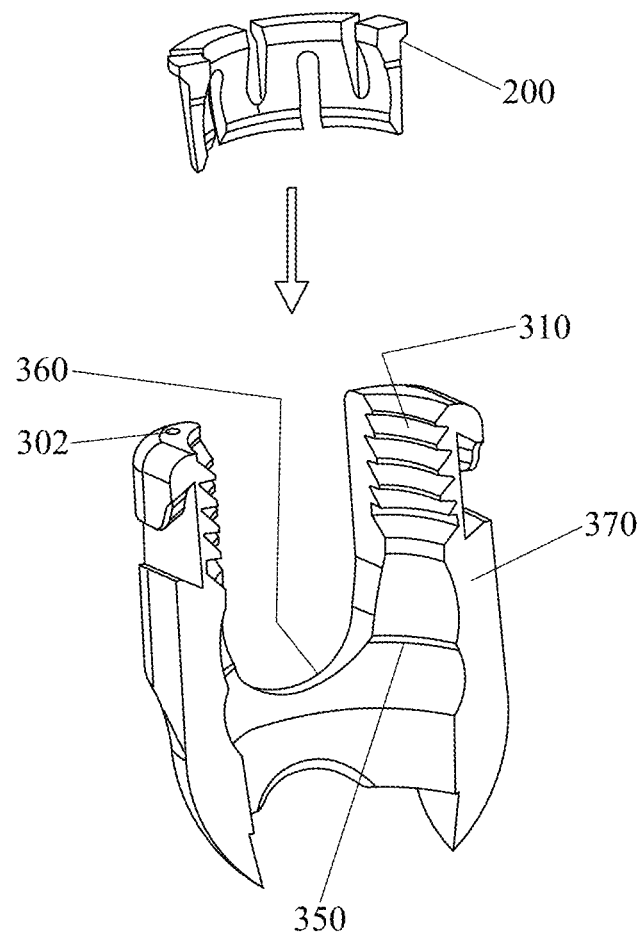
FIGS. 16A-16G are three-dimensional perspective cross-sectional illustrations which show sequential steps in the assembly of a screw of an embodiment.

Referring now to FIG. 16A through FIG. 16G, it is possible that the following assembly sequence may be used to assemble the described components:

1. As is shown in FIG. 16A, the proximal portion 370 of the movable head 300 is provided without its distal portion 380.

Figure 16B:
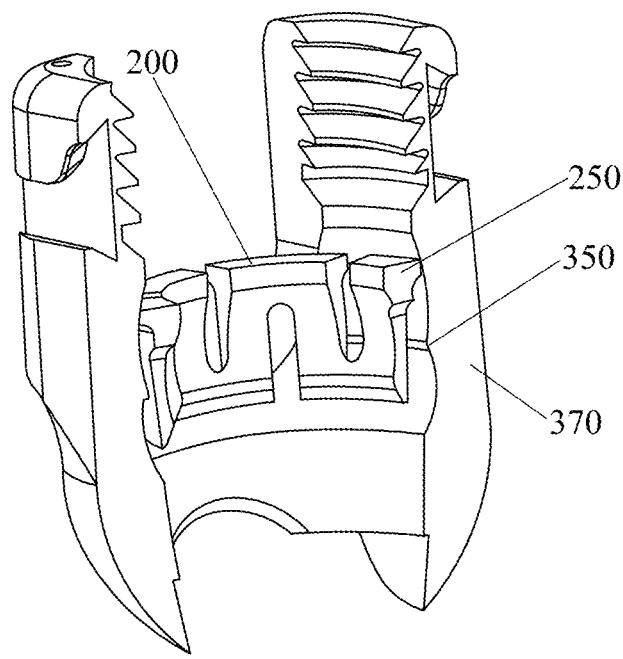

2. Referring now to FIG. 16B, the collet 200 is introduced through the proximal end 302 of the proximal portion 370 of the movable head 300. The collet 200 is brought partially into the movable head 300 but is stopped before external lip 250 of the collet 200 passes the internal lip 350 of the movable head 300. This may be termed a screw-receiving position of the collet 200.

Figure 16C:
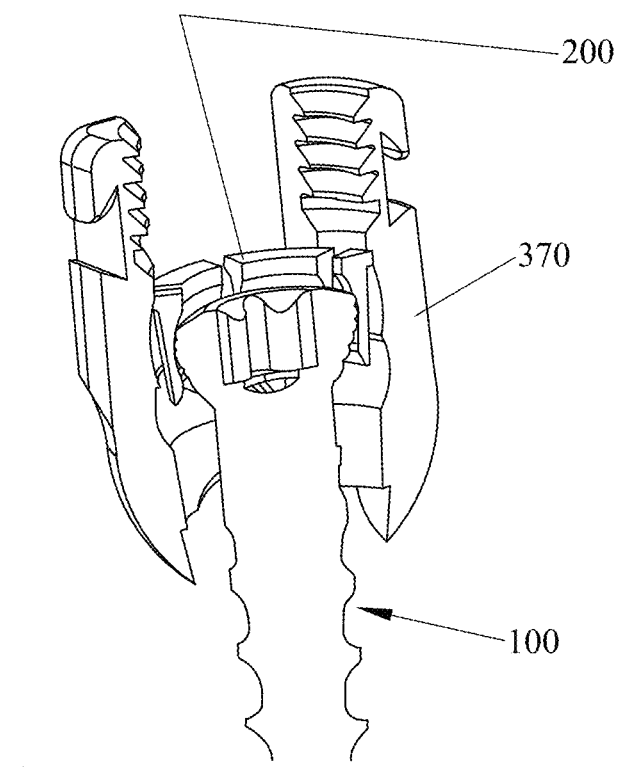

3. With reference to FIG. 16C, with the collet 200 in the screw-receiving position, the screw head 130 is brought up through the distal end 304 opening of the movable head 300. The screw head 130 is brought into the collet internal space where it is received, which requires some elastic deformation of the collet 200.

Figure 16D:
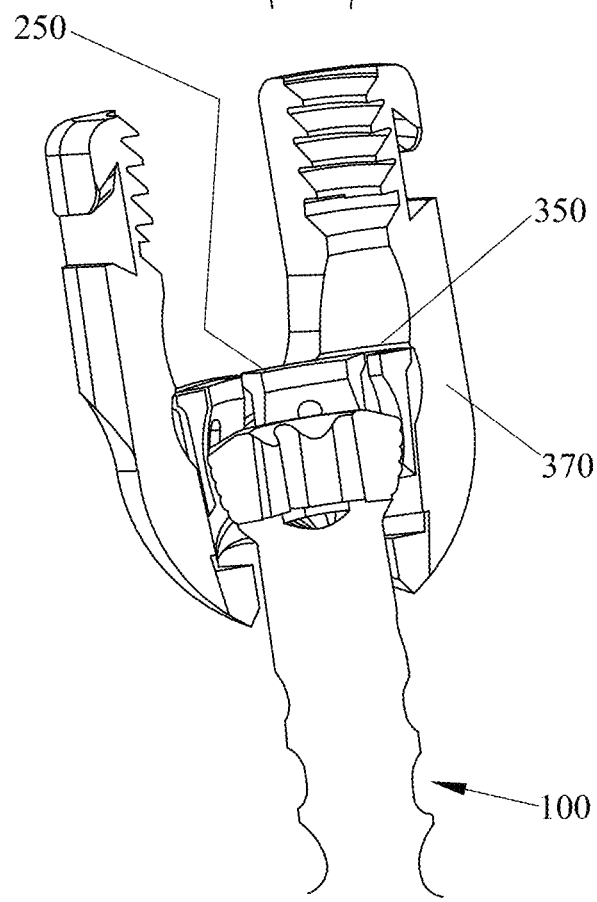

4. Referring now to FIG. 16D, the collet 200, with the screw head 130 already received inside it, is then advanced farther distally into the movable head 300 so that the external lip 250 of the collet 200 passes the internal lip 350 of the movable head 300, and the collet 200 reaches its assembled position, in which the collet external lip 250 is more distal than the internal lip 350.

Figure 16E:
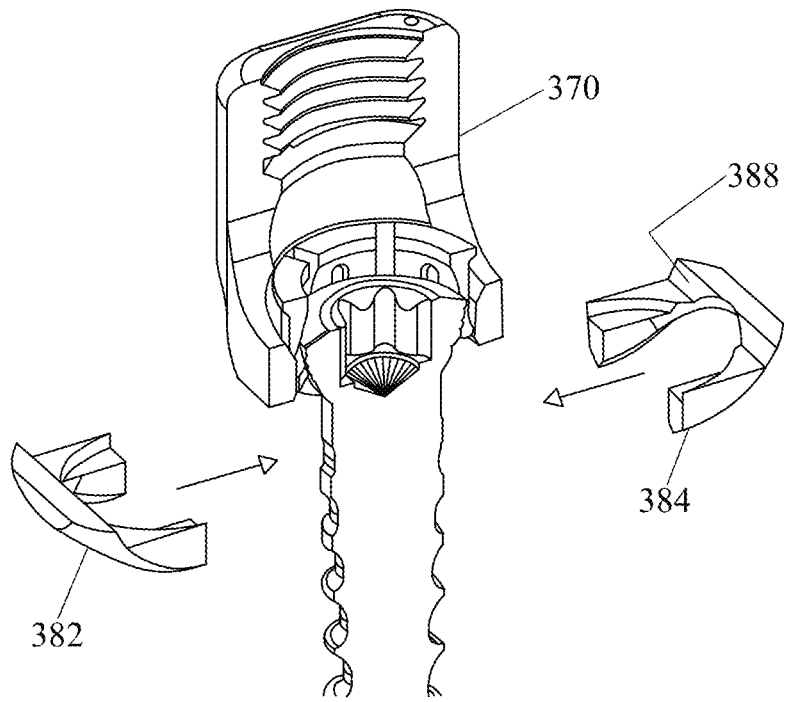

5. Referring to FIG. 16E, sub-motion-limiters 382, 384 are brought into position at the distal end of the movable head 300. Because the bottom shoulder has sub-motion-limiters 382, 384, one sub-motion-limiter can be brought in from each of two opposed directions. If the sub-motion-limiters and the main body of the movable head 300 are related by means of a dovetail or mechanical interlocking relationship, this feature may provide mechanical support. For clarity of illustration, the proximal portion 370 and the screw 100 are shown sectioned, but the sub-motion-limiters 382, 384 are shown in their entirety. It is also illustrated in FIG. 16E that the sub-motion-limiters 382, 384 may have a stop feature 388 that cooperates with the screw shaft 110 to limit the motion of the screw shaft 110 relative to the movable head 300.

Figure 16F:
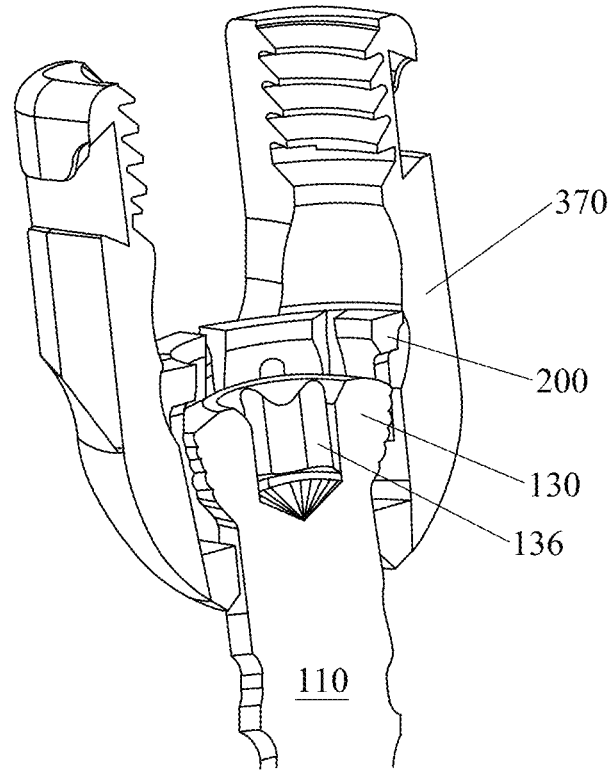

6. In FIG. 16F, the sub-motion-limiters 382, 384 are joined to the main body of the movable head 300, such as by welding. At this stage of assembly, as described elsewhere herein, there may be friction such that the movable head 300 may be placed in any desired position relative to the screw 100, within the range of permitted motion, and will remain in that position at least against gravitational forces acting on the various parts of the screw assembly (i.e., the individual weight of the various parts), in any orientation. The friction may be greater than what is needed simply to maintain a position against gravitational forces.

Figure 16G:
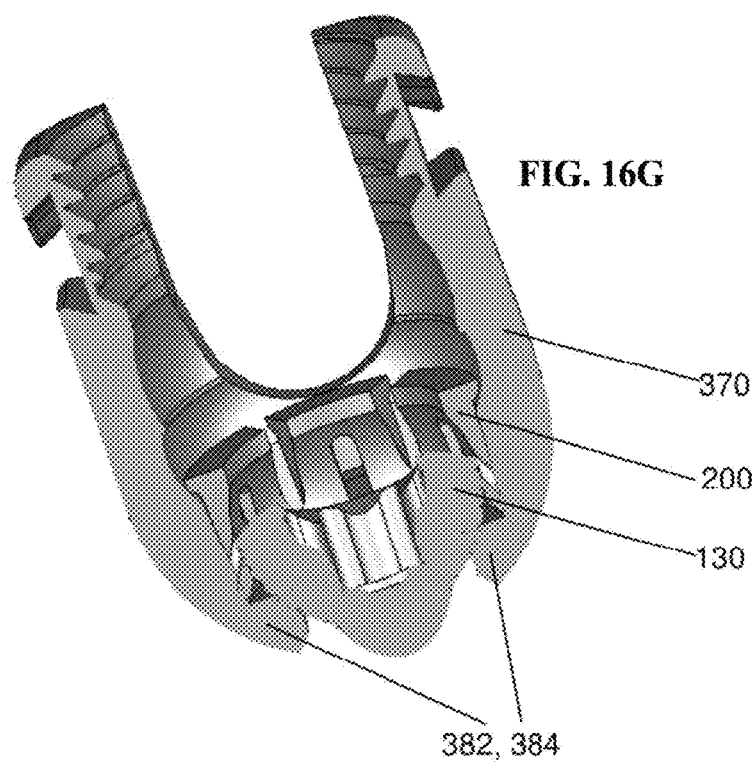
Figure 17A:
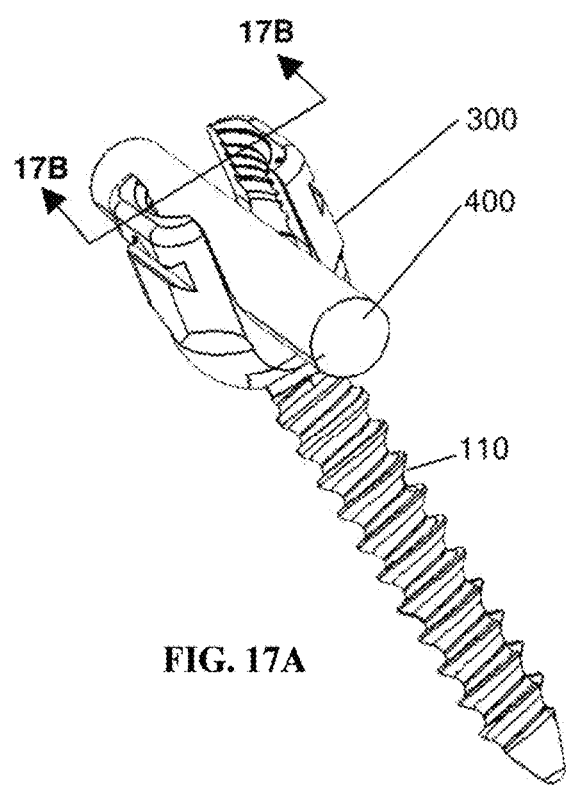
FIG. 17A is a three-dimensional perspective view of a screw assembly of an embodiment, together with a spinal rod.
Figure 17B:
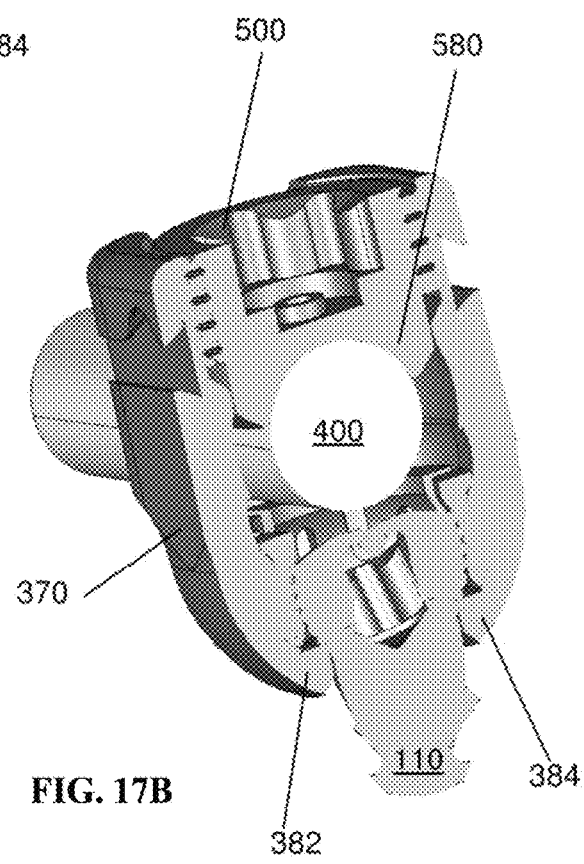
FIG. 17B is a cross-section of FIG. 17A, along 17B-17B.

7. Next, referring now to FIG. 16G and also to FIGS. 17A and 17B, when the assembly is being implanted into a patient and a spinal rod 400 is being clamped by tightening of set screw 500 pressing against spinal rod, the spinal rod may press against the top of the collet 200, which may further urge the collet 200 or the screw head 130 or both into a final-tightened position, which may be advanced farther distally within the movable head 300 as compared to the assembled position. In FIG. 16G, for clarity of illustration, the spinal rod 400 is not shown. The position of the collet 200 along the proximal-distal direction can be judged, for example, by the position of the collet lip 250 relative to the bottom of the U-trough 360 or relative to the internal lip 350. These positions differ from FIG. 16F to FIG. 16G. The final clamped position is also illustrated in FIGS. 17A and 17B. A detail concerning the final-tightened position relates to the collet 200 having an angular position around its own longitudinal axis 240, which may be arbitrary, with respect to the movable head 300. More specifically, it is possible either that the spinal rod 400 presses against the external lip 250 of the collet 200, or that the spinal rod presses against the gap 210 in the external lip 250 of the collet 200. The choice of lip contact or gap contact can make a slight difference in the actual axial position of the collet 200, along its own axis 240, when the whole assembly is tightened. However, the difference will not be very large. In the tightened position as illustrated, the spinal rod 400 may bear against the lip 250 of the collet 200 and may be out of contact with the screw head 130. Clamping of the screw head 130 may be achieved by frictional gripping of the collet 200 against the screw head 130. However, depending on design details, other options may also be possible. Other assembly sequences are also possible. For example, there is some freedom as to when one performs the step of advancing the collet 200, with the screw head 130 already received inside it, farther distally into the movable head 300 so that external lip of the collet 200 passes internal lip 350. Such step could be performed either before or after assembly of the sub-motion-limiters 382, 384 onto proximal portion 370.

As illustrated in FIGS. 14A, 14B and 15, the sub-motion-limiters 382, 384 (or distal portion 380) may have a recess therein for receiving a portion of the collet 200. The collet 200 need not bear against the recess in distal portion 380 or sub-motion-limiters 382, 384, but the recess 394 may nevertheless be provided to allow space that can be occupied by a portion of the collet 200.

Apparatus in Tightened Configuration

Referring now to FIGS. 17A and 17B, there is further shown the assembly of the components of all previous Figures. Referring to FIG. 17A, there is shown the previous assembly having the screw 100, the collet 200 and the movable head 300, together with a segment of a rod 400, such as a spinal rod, seated in the movable head 300. As illustrated, a set screw 500, and possibly saddle 580, is tightened against rod 400, rod 400 bears against the proximal surface of the collet 200. It is possible that there may be differences in position of the collet 200 between a nominal assembled configuration and a final tightened configuration. It is possible that in the final tightened configuration, the collet 200 may be more deeply (more distally) located within the movable head 300 than is the case for the nominal assembled configuration. For example, between the nominal assembled configuration and the final tightened configuration, the collet 200 may undergo some elastic deformation. However, this is dependent on design details and is optional.

As the rod 400 approaches or touches the bottom of the U-trough 360, it is possible that the rod 400 may also touch the bottom of the U-trough 360, but that is optional and depends on design details.

As illustrated in FIG. 17B, the rod 400 does not touch the upper surface of the screw head 130. However, these are merely one of several available design options. In general it is possible that, in a tightened condition, the rod 400 might touch any or all of: the bottom of the U-trough 360; the proximal surface of the collet 200; and the upper surface of the screw head 130; or more than one of these in any combination thereof.

Figure 18A:
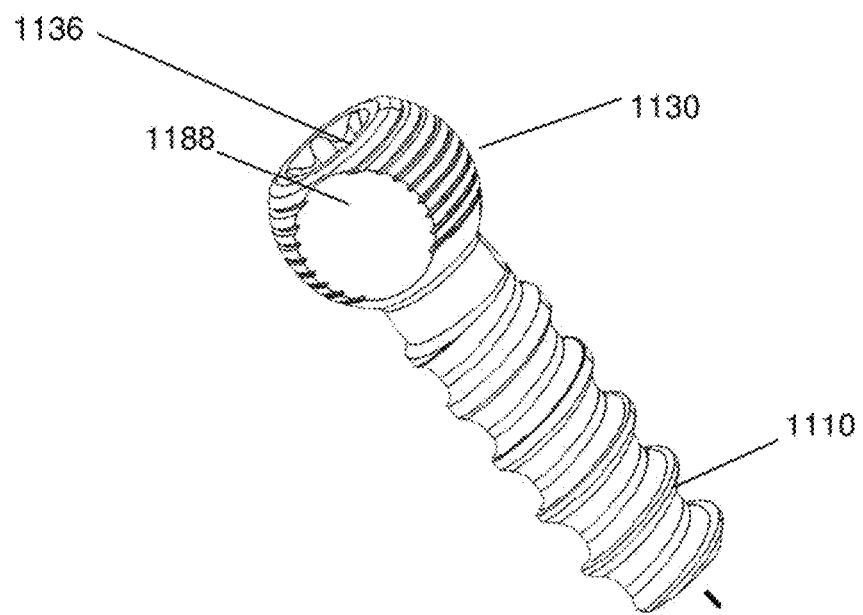
FIG. 18A is a three-dimensional perspective view of a screw of another disclosed embodiment
Figure 18B:
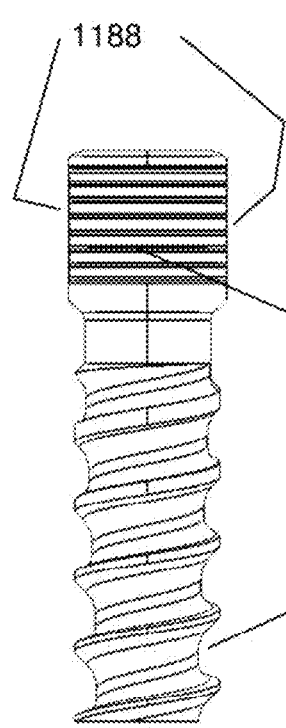
FIGS. 18B and 18C are side views of the embodiment shown in FIG. 18A.
Figure 18C:
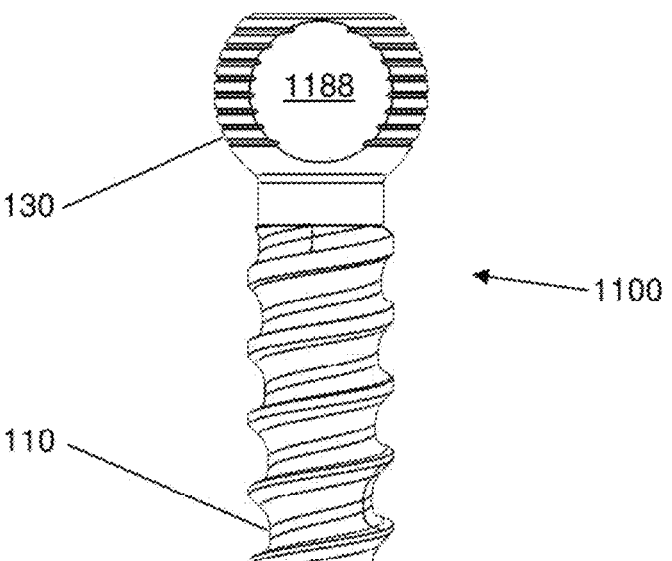

Referring now to FIGS. 18A-18C, yet another embodiment may achieve uniplanar motion using a different embodiment than as previously disclosed in which the screw head possesses a pair of flat surfaces rather than being generally axisymmetric about its own centroidal axis as in the embodiment previously described. This alternate embodiment may be provided with a screw 1100. The screw 1100 may have a shaft 1110 and a screw head 1130 integral with or joined to the shaft 1110. The screw 1100 may have a longitudinal axis 1140.

In this embodiment, the screw head 1130 may have a portion of a sphere but furthermore may have two planar surfaces 1188 that may be opposed to each other. The planar surfaces 1188 may be parallel to each other and may be equally spaced on opposite sides of the longitudinal axis of shaft of the screw 1100.

Referring now to FIGS. 19A-19D and 20, the embodiment may further provide a movable head 1300. The movable head 1300 may have a proximal portion 1700 and a distal portion 1800 that may be connected to or joined to each other or may be suitable to attach to each other.

The proximal portion 1700 of the movable head 1300 may have a U-trough 1360 therethrough suitable to receive a spinal rod. The proximal portion 1700 of the movable head 1300 may also have an axial opening 1365 extending from its proximal end to its distal end. The axial opening 1365 may merge with the open space of the U-trough 1360. The axial opening 1365 may be large enough for the screw head 1130 to pass through the distal end of proximal portion 1700. The axial opening 1365 may be non-circular. Portions of the axial opening 1365 may be suitable to interact with the planar surfaces 1188 of the screw head 1130.

The distal portion 1800 of the movable head 1300 may have an internal surface that is dimensioned suitably to bear against and retain the distal-facing surface of the screw head 1130. The distal portion 1800 of the movable head 1300 may have an opening 1865 therethrough, through which the screw head 1130 is unable to pass. This opening 1865 may be circular as illustrated, although it could be non-circular if desired. The opening 1865 facing distally may have a chamfer or other transitional feature. The distal portion 1800 of the movable head 1300 may be such as to limit angulation of the screw 1100 with respect to the movable head 1300. The distal portion 1800 of the movable head 1300 may be axisymmetric about its own centroidal axis.

Referring now to FIGS. 21A and 21B, the apparatus may further have a force-transmitting cap 1900. The force-transmitting cap 1900 may have a distal surface 1920 that is at least partially spherical and compatible with the spherical external surface of the screw head 1130. The force-transmitting cap 1900 may have a proximal surface 1930 that is at least partially cylindrically compatible with a cylindrical spinal rod. The force-transmitting cap 1900 may possess a hole 1965 therethrough that generally connects the distal surface 1920 and the proximal surface 1910. The hole 1965 may be of larger diameter or cross-sectional dimension than an instrument-receiving interface 1136 in the screw 1100. The force-transmitting cap 1900 may have side surfaces 1950a, 1950b that may be substantially flat and parallel and suitable to fit between corresponding surfaces of the proximal portion of the movable head 1300. The force-transmitting cap 1900 may further be provided with a shoulder 1642, and the proximal portion of the movable head 1300 may possess a recess suitable to receive the shoulder 1642 of force-transmitting cap 1900. The force-transmitting cap 1900 may in some dimension be larger than axial opening through the distal portion 1800 of the movable head 1300. As a result, when the apparatus is fully assembled, the force-transmitting cap 1900 may be trapped and unable to exit proximally because of the shoulder causing it to be trapped within the proximal portion 1400 of the movable head 1300, and unable to exit distally because of being trapped by the distal portion 1800 of the movable head 1300.

When the apparatus is assembled and implanted in a patient, the various components may be such that a set screw engages threads in the proximal portion 1700 of the movable head 1300 and presses on the spinal rod, which in turn presses on the force-transmitting cap 1900, which in turn presses on the screw head 1130. Forces from the screw head 1130 are in turn reacted by the distal portion 1800 of the movable head 1300, which is in turn connected to the proximal portion 1700 of the movable head 1300.

Referring now to FIG. 22A and FIG. 22B, there are shown cross-sections of the assembled apparatus. FIG. 22A is a cross-section taken in a plane that includes the spinal rod 1400, and FIG. 22B is a cross-section in a plane perpendicular to the spinal rod 1400. In FIG. 22A and in FIG. 22B, it can be seen that force-transmitting cap 1900 presses on the screw head 1130. It can be noted that some of the force-transmitting cap 1900 may protrude slightly into the space within the U-trough 1360, beyond the interior surface itself of the U-trough 1360 itself. This enables the spinal rod to exert force directly on the force-transmitting cap 1900, which in turn exerts force on the screw head 1300, to lock the position of the screw 1100 with respect to the movable head 1300. In FIG. 22B, the flat sides 1188 of the screw head 1130 are also visible. Flat sides 1188 interact with corresponding flat surfaces in proximal portion 1700 to limit angulation of the screw head 1130 in a certain degree of freedom of motion.

Referring now to FIG. 23, there is illustrated an assembly omitting the force-transmitting cap 1900. This illustrates the shape into which the force-transmitting cap 1900 fits. Referring now to FIG. 24, there is illustrated distal portion 1800 and the screw 1100. This illustrates that the distal portion 1800 traps the screw head 1130.

FIG. 25A-25D show steps of assembly of the apparatus of this embodiment. FIG. 25A shows only the proximal portion 1700 of the movable head 1300 as a first step of assembly. As a second step of assembly, FIG. 25B shows the proximal portion 1700 of the movable head 1300, together with the force-transmitting cap 1900. It can be noted that the force-transmitting cap 1900 is introduced into proximal portion 1700 through the distal end of proximal portion 1700, and is not able to travel all the way through the proximal portion 1700, so that it later becomes trapped within the assembly. As a third step of assembly, FIG. 25C shows the proximal portion 1700 of the movable head 1300 together with the force-transmitting cap 1900 and the screw 1100. As a final step of assembly, FIG. 25D shows the components already illustrated in FIG. 25C, together with the distal portion 1800 joined to proximal portion 1700. The joining of the distal portion 1800 to proximal portion 1700 traps the screw head 1130 and also traps the force-transmitting cap 1900.

Alternate Design of Motion Limiters

Referring now to FIGS. 26-27D, there is illustrated another embodiment of the invention. FIG. 26 shows an assembly comprising a screw 2100 including a screw shaft 2110, a collet 2200, and movable head 2300. The movable head 2300, shown in more detail in FIGS. 27A-27D, may contain within itself two motion limiters 2382, 2384. The first motion limiter 2382 and the second motion limiter 2384 may occupy respective grooves 2372, 2374 in the movable head 2300. The grooves 2372, 2374 may have a longitudinal axis that may be generally parallel to a longitudinal axis of the U-trough 2360 that extends through the movable head 2300, and may also be generally parallel to the longitudinal axis of the spinal rod 400 that would be received within the U-trough 360 of the movable head 300. As illustrated, there is one groove 2372, 2374 on each side of the mid-plane of the movable head 2300, and the two grooves 2372, 2374 are substantially parallel to each other. Groove 2372 and groove 2374 may be symmetric about a common plane to each other.

A first motion limiter 2382 may be generally long and located within groove 2372 and located entirely on one side of the plane that is a mid-plane of the movable head 2300, corresponding to the spinal rod 400. A second motion limiter 2384 may be generally long and located entirely on the other side of the plane in groove 2374. The first motion limiter 2382 and the second motion limiter 2384 may be symmetric about a common plane to each other.

The respective grooves 2372, 2374 in the movable head 2300 may comprise dovetail features, and the motion limiters 2382, 2384 may have external taper features corresponding to a dovetail joint. In particular, the grooves 2372, 2374 may be wider at the top than at the bottom (in the orientation shown), and the motion limiters 2382, 2384 may be wider at the top than at the bottom (in the orientation shown). The taper angle of the dovetail feature of the groove 2372, 2374 is illustrated in FIG. 27B, and a taper angle of the motion limiter 2382, 2384 is illustrated in FIG. 27C. These two taper angles may be equal to each other, although it is not necessary that they be exactly equal to each other.

As a result, even when the motion limiters 2382, 2384 are merely in place within the grooves 2372, 2374 of the movable head 2300 without being physically joined to the movable head 2300, the motion limiters 2382, 2384 may be physically trapped within the grooves 2372, 2374. In particular, the motion limiters 2382, 2384 may be trapped within the dovetail grooves 2372, 2374 in such a way as to prevent motion of the motion limiters 2382, 2384 downward in the illustrated orientation. The motion limiters 2382, 2384 may furthermore be secured within the grooves 2372, 2374 by a weld (not illustrated), or alternatively by other joining means such as adhesive. A weld could be created, such as by laser welding, electron beam welding or any other suitable form of welding, at any suitable location where an edge or surface of motion limiter 2382, 2384 is close to an edge or surface of movable head 2300, and where such edges or surfaces are physically accessible for deposition of energy during welding. Such welding may be performed either with or without adding of additional material during welding. Thus, there may be a primary retention mechanism or load path that comprises the interaction between the grooves 2372, 2374, and the motion limiters 2382, 2384 in the manner of physical trapping so as to resist or prevent downward motion of the motion limiters 2382, 2384 with respect to the movable head 2300, and there may be a secondary retention mechanism that comprises the weld or the joining of the motion limiters 2382, 2384 to the movable head 2300. The weld or adhesive or joining or similar securing mechanism may anchor the motion limiters 2382, 2384 in place with respect to the longitudinal direction of the groove 2372, 2374 and the longitudinal direction of the motion limiters 2382, 2384. The weld or adhesive or joining or similar securing mechanism may further serve some role, although not necessarily a major role, in the actual transfer of load between the motion limiter 2382, 2384 and the movable head 2300.

FIG. 27A shows a movable head 2300 containing two motion limiters 2382, 2384, in a three-dimensional view from slightly below the movable head 2300. FIG. 27B is an illustration similar to FIG. 27A, except that the motion limiters 2382, 2384 are removed. In FIG. 27C there are illustrated two motion limiters 2382, 2384 as they would be positioned in the assembled movable head 2300, but for clarity of illustration the body of the movable head 2300 is omitted so that only the two motion limiters 2382, 2384 are shown. In this illustration, the dovetail angles of each motion limiter 2382, 2384 are labeled, and they correspond to complementary features of the dovetail features of the grooves 2372, 2374. Finally, FIG. 27D shows a single motion limiter 2372 in a different orientation suitable to show certain features of the motion limiter 2372. In particular, it can be noted that motion limiter 2372 may have, and is illustrated as having, a flat edge 2388. This edge 2388 or a corner associated with it may interact with shaft 2110 of screw 2100.

For further illustration, FIG. 27E and FIG. 27F show the movable head 2300 together with one motion limiter 2384 that is in place and the other motion limiter 2382 that is displaced along the direction of motion according to which motion limiter 2382 would be advanced into slot 2372. In FIG. 27E, which is a perspective view, the viewing direction is along the direction of advancement, and motion limiter 2382 is displaced far enough back to provide an apparent difference in size due to perspective. In FIG. 27F, which is a view more from below, motion limiter 2382 is displaced only to the point where it begins to make contact with movable head 2300.

One or both of the motion limiters 2382, 2384 may have an edge 2388 that faces the shaft 2110 of the screw 2100, and that edge 2388 may determine the geometry of motion limitation imposed on the screw 2100. As illustrated in FIG. 28, if there are two motion limiters 2382, 2384 and both of them have screw-shaft-facing edges that are substantially straight and are located close to the screw shaft 2110, then the allowable range of motion of the shaft 2110 of the screw 2100 may be substantially within a plane as illustrated, i.e., what is referred to as uniplanar. It can further be appreciated that, if there are two motion limiters 2382, 2384 and both of them have screw-shaft-facing edges that are substantially straight and have a certain clearance with respect to the screw shaft 2110, then the allowable range of motion of the shaft 2110 of the screw 2100 will be approximately uniplanar with a little bit of play perpendicular to the plane of the uniplanar motion.

In various illustrations herein, there are illustrated two different kinds of movable head. One difference is a difference in the external shape. The movable head design shown in FIG. 29A has an external cross-section that is roughly cylindrical in cross-section (taken perpendicular to the longitudinal axis of the movable head), and the movable head design shown in FIG. 29B has an external cross-section that is roughly rounded-square in cross-section (taken perpendicular to the longitudinal axis of the movable head). Also, the movable head design shown in FIG. 29A has an instrument interface feature that is a simple racetrack-shaped recess 2391, while the movable head design shown in FIG. 29B has an instrument interface that comprises a dovetail groove 2390A, 2390B (not to be confused with the dovetail groove 2372, 2374 that receives the motion limiters 2382, 2384). In practice, the movable head design shown in FIG. 29A might be manufactured of a titanium alloy, while the movable head design shown in FIG. 29B might be manufactured of a stainless steel alloy.

Most generally, there could be any combination of external cross-section shape of the movable head, any design for an instrument interface to the movable head, any choice of material, and any choice as far as configuration of limiters (described elsewhere herein).

D-Planar Screw

Referring now to FIGS. 30A-30D and FIGS. 31A, 31B, in an embodiment of the invention, there may be provided a movable head 3300 assembled to a screw 3100 having shaft 3110 that defines a space of allowable positions for the screw shaft that has a boundary that is not a simple circular boundary. Such perimeter of the boundary that defines or limits the motion of the screw shaft 3110 with respect to the movable head 3300 may be defined by a portion that is a straight line and a portion that is a curve. Such a curve may be a portion of a circle. Such a range of allowable positions of the screw shaft is illustrated in FIGS. 31A and 31B.

Such a range of motion may be achieved by a movable head 3300 that has a motion-limiting edge such that for a portion of the motion-limiting perimeter there is provided a motion limiter 3384, which may provide a straight-line limiting edge if desired, while for another portion of the on the opposite side of the mid-plane, the motion of the screw shaft 3110 with respect to the movable head 3300 may be defined by an edge that is or includes a portion of a circle.

In particular, the straight-line portion of the motion-defining edge on one side of the mid-plane of the movable head 3300 may be defined by a motion limiter 3384, while the portion of the motion-limiting edge that is a portion of a circle may be defined by the body of the movable head 3300 with no presence of a separate motion limiter. The motion limiter 3384, which may occur on only one side of the movable head 3300 but not the other side, may be similar to the motion limiter 2382, 2384 described elsewhere herein.

It is also possible that the motion limiter 3384 (or similarly, 2382, 2384), which has been illustrated here as having an edge that is straight, could have an edge that is some other shape. The same may be true for the sub-motion-limiters 382, 384 described elsewhere herein.

In FIG. 30, what is illustrated as the D-planar design has a movable head that substantially corresponds to the first design, FIG. 29A, rather than the second design in FIG. 29B. However, it is to be understood that the D-planar features of FIG. 30 could similarly be used with the second design or with any other design details of the movable head 3300.

FIG. 31A and FIG. 31B illustrate a range of possible positions of the shaft 3110 with respect to the movable head 3300, for the D-planar design of FIG. 30.

In any embodiment of the invention, there may be provided a collet 3200 as illustrated in FIG. 32A and FIG. 32B. In understanding this collet 3200, it may be helpful to understand that in a movable-head screw that contains a collet surrounding the spherical screw head, it is possible that the angular orientation of collet 3200 with respect to movable head 3300, with respect to the longitudinal axis of the collet 3200, may be unknown. Even if the assembly may be assembled with the collet in a known angular orientation, it may be unclear if the collet will always remain in that same orientation. With such angular orientation being uncertain, it is possible that in a final installed and tightened situation, a spinal rod 400 may rest on the solid portion of the lip 3250, or alternatively it is possible that a spinal rod 400 may sit on the gap that may occur at a slot in the collet. These two different situations, either of which could possibly occur, could possibly result in a difference in the physical location of the spinal rod relative to the movable head 3300, and even possibly a difference in the path of load transfer from the spinal rod 400 to the movable head 3300.

For the collet as illustrated in FIG. 32A-32B, the collet may have at one end a lip 3250, or, whether or not a lip is present, may have a flat surface at one end. As illustrated in FIG. 32A, the collet may be provided with slots 3212 entering from a first or proximal end of the collet and slots 3214 entering from a second or distal end of the collet. When viewed looking at the lip 3250 from above the collet, there may be seen gaps in the lip or flat surface. The number of those gaps may be an odd number, so that it is not possible for the spinal rod to simultaneously contact gaps at one location on the lip 3250 of the collet 3200 and also a diametrically opposed location on lip 3250.

Also, as best illustrated in FIG. 32B, the gaps 3212 at the end of the collet that has the lip 3250 may be oriented in a non-radial direction. It is further possible that the width of the gap 3212, the thickness of the lip 3250 in a radial direction, and the angular orientation of the gap 3212, interact with each other such that any radial line (representing a line of possible contact with spinal rod 400) has to intersect at least a portion of the lip 3250.

The number of slots entering from the first end may be different from the number of slots entering from the second end. In particular, the number of slots 3214 entering from the distal end or the end that does not have the lip 3250 may be greater than the number of slots 3212 entering from the proximal end or the end that has the lip 3250 or flat surface. For example, for the number of slots 3214 entering from the end that does not have the lip 3250 may be twice the number of slots 3212 entering from the end that does have the lip 3250.

Of course, the collet 3200 described herein could be used with any of the screw embodiments described herein. Although embodiments of the invention have been illustrated comprising a collet that provides friction to retain positioning of the screw shaft with respect to the movable head, it would also be possible to create a similar screw assembly that does not have a collet or friction by omitting the collet.

Embodiments of the invention have been described herein having a dovetail relationship between the motion limiter and the movable head, specifically the groove within the movable head. It can be understood that a dovetail joint is just one of various possible geometries that allow the motion limiter to slide in to the movable head. For example, it is possible that a step joint having generally perpendicular sides, which may be referred to as a shelf or shelf joint, could be used. More generally, it is simply necessary that a proximal dimension of the motion limiter or sub-motion-limiter be greater than a corresponding distal dimension of the groove in which the motion limiter or sub-motion-limiter occupies. This provides a mechanical support or interlock to prevent the motion limiter or sub-motion-limiter from being urged out of the movable head. As described elsewhere herein, such mechanical support can be supplemented by a joining such as welding.

It can be understood that in an embodiment such as the embodiment of FIGS. 1-17 and the embodiments of FIGS. 26-32C), the screw 100 is able to be rotated arbitrarily about its own longitudinal axis 140 with respect to the movable head 300. This means that the angular rotation of the screw 100 into bone can be selected arbitrarily, and therefore the elevation of the screw head 130, with respect to bone into which the screw 100 is the screwed, can be adjusted or chosen in a continuous manner. For some embodiments of the present invention (such as the embodiment of FIG. 1-17 and the embodiments of FIGS. 26-32C), it is possible to adjust the elevation of the screw head 130, relative to the local bone, in a continuous manner, while still providing the restricted type of motion of the movable head relative to the screw shaft as described herein. Any screw described herein may be cannulated, such as for accommodating a K-wire or for delivery of a liquid such as cement to the interior bone region. If cannulation of the screw is provided, fenestration of the walls of the screw is also possible.

The foregoing description of structures and methods has been presented for purposes of illustration. It is not intended to be exhaustive or to limit the invention to the precise steps and/or forms disclosed, and obviously many modifications and variations are possible in light of the above teaching. Features described herein may be combined in any combination. Steps of a method described herein may be performed in any sequence that is physically possible. It is understood that while certain forms of a uniplanar the screw have been illustrated and described, it is not limited thereto and instead will only be limited by the claims, appended hereto. All referenced documents are incorporated by reference herein.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The invention claimed is:

1. A movable head for a spinal screw apparatus, comprising:
   a top portion and a bottom portion and a concave interior, wherein said concave interior is configured to receive a screw head, wherein said movable head has a trough through said top portion, wherein said trough has an axis; and
   wherein said movable head has a bottom opening through said bottom portion, wherein said bottom opening has a contact perimeter shape, wherein said concave interior extends upwardly from said contact perimeter shape towards said top portion, wherein said contact perimeter shape comprises a curved portion intersecting said concave interior and a single straight portion that is exterior to said concave interior and connects with said curved portion.

2. The movable head of claim 1 wherein said single straight portion of said contact perimeter shape is parallel to said axis.

3. A spinal screw apparatus comprising the movable head of claim 1 and a screw, wherein said screw comprises a shaft and a screw head attached to said shaft, wherein said screw head further comprises a portion of a sphere.

4. The movable head of claim 1 wherein a length of said single straight portion is less than a diameter of said curved portion.

5. The movable head of claim 1 wherein said single straight portion lies in a first plane and at least a portion of said curved portion lies in a second plane, and said first plane and said second plane are different from each other.

6. The movable head of claim 5 wherein said first plane and said second plane are parallel to each other.

7. The movable head of claim 1 wherein single straight portion is an edge of a motion limiter.

8. The movable head of claim 1 wherein said single straight portion is located opposite said curved portion.

9. A movable head, comprising:
   a body having an opening therethrough, said opening having an opening longitudinal axis, said body having a proximal end and a distal end;
   said body further comprising an internal surface defining an internal cavity having a distal end opening perimeter adjacent said distal end;
   wherein said body comprises a proximal component and at least one distal component joined to said proximal component, each of said distal component and said proximal component defining at least a portion of said distal end opening perimeter;
   wherein said distal component has a mechanical interlock with said proximal component; and wherein said distal end opening perimeter adjacent said distal end comprises a single straight line segment.

10. The moveable head of claim 9 wherein said distal component includes said single straight line segment.

11. The movable head of claim 9 wherein said mechanical interlock comprises a dovetail joint.

12. The movable head of claim 9 wherein said mechanical interlock comprises a shelf joint.

13. The movable head of claim 9 wherein said distal end opening perimeter includes a curve, wherein said curve is a portion of a circle.

14. The movable head of claim 9 wherein said distal component is a motion limiter or a sub-motion-limiter.

* * * * *